United States Patent [19]

Angehrn et al.

[11] Patent Number: 6,150,350

[45] Date of Patent: Nov. 21, 2000

[54] ANTIMICROBIAL COMPOSITIONS

[75] Inventors: Peter Angehrn, Böckten, Switzerland; Ingrid Heinze-Krauss, Schliengen, Germany; Malcolm Page, Basel, Switzerland; Hans G. F. Richter, Grenzach-Wyhlen, Germany

[73] Assignee: Hoffman-la Roche Inc., Nutley, N.J.

[21] Appl. No.: 09/138,866

[22] Filed: Aug. 24, 1998

[30] Foreign Application Priority Data

Sep. 15, 1997 [EP] European Pat. Off. ............. 97115997

[51] Int. Cl.[7] ..................... A61K 31/545; C07D 501/00; C07D 487/00; C07D 499/00
[52] U.S. Cl. ................... 514/202; 514/206; 540/222; 540/225; 540/302; 540/310
[58] Field of Search ..................... 514/202, 206; 540/222, 225, 310, 302

[56] References Cited

U.S. PATENT DOCUMENTS

| 5,464,616 | 11/1995 | Noguchi et al. | 424/114 |
|---|---|---|---|
| 5,644,053 | 7/1997 | Hubschwerlen et al. | 540/310 |

FOREIGN PATENT DOCUMENTS

| 384 410 | 2/1990 | European Pat. Off. . |
|---|---|---|
| 640 607 | 8/1994 | European Pat. Off. . |
| 620 255 | 10/1994 | European Pat. Off. . |
| 841 339 | 10/1997 | European Pat. Off. . |
| 92/04353 | 3/1992 | WIPO . |
| 96 26943 | 9/1996 | WIPO . |

OTHER PUBLICATIONS

Derwent Abstract No. JP 2279627.
Hohl et al., Abstracts of the Interscience Conference on Antimicrobial Agents and Chemotherapy, vol. 36, p. 125 (1996).
Jones et al., Diagnostic Microbiology and Infectious Disease, vol. 32, No. 2, p. 85–94 (1998).

*Primary Examiner*—Gary Geist
*Assistant Examiner*—Everett White
*Attorney, Agent, or Firm*—George W. Johnston; Patricia S. Rocha-Tramaloni; Eileen M. Ebel

[57] ABSTRACT

The invention relates to antimicrobial compositions comprising a combination of (1) a therapeutically effective amount of a compound of formula I

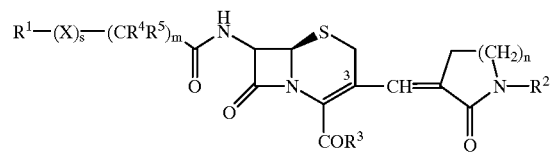

with (2) a second ingredient selected from carbapenem antibiotics or with β-lactamase inhibitors, to the use of the compositions for producing a medicament for the treatment and prophylaxis of infectious diseases, including MRSA infections, and to pharmaceutical compositions containing the combination.

17 Claims, No Drawings

ANTIMICROBIAL COMPOSITIONS

BACKGROUND OF THE INVENTION

The present invention relates to antimicrobial pharmaceutical compositions comprising a combination of a compound of formula (I) with a carbapenem antibiotic or with a β-lactamase inhibitor, to the use of the compositions for producing a medicament for the treatment and prophylaxis of infectious diseases, including MRSA infections, and to pharmaceutical compositions containing the combination.

The extensive use of β-lactam antibiotics during the last decades result in a considerable increase of pathogens resistant to this class of antibiotics. A major threat are infections caused by Methicillin resistant Staphylococcus aureus (MRSA). Various strains of MRSA have been reported to be resistant not only to β-lactams but also to many other antimicrobial agents, including aminoglycosides, erythromycin, chloramphenicol and quinolones.

The compounds of formula (I), also known as vinyl-pyrrolidinone cephalosporin derivatives and their preparation are described in the European Patent Application 841 339, published May 13, 1998. These compounds exhibit a high antimicrobial activity against non-β-lactamase producing strains of MRSA. In β-lactamase-producing strains of MRSA partial hydrolysis of vinyl-pyrrolidinone cephalosporins can occur.

It has now been found that a combination of vinyl-pyrrolidinone cephalosporins of the formula I with β-lactamase inhibitors like, e.g. clavulanic acid, Tazobactam, Sulbactam or (Z)-(2S,3S,5R)-3-(2-cyanoethenyl)-3-methyl-4,4,7-trioxo-4-thia-1-aza-bicyclo[3.2.0]heptane-2-carboxylic acid (a compound as described in the European Patent Application EP-A-0 640 607) prevents these compounds from being hydrolyzed by staphylococcal β-lactamase thus, resulting in a synergistic effect.

Carbapenems like, e.g. Imipenem or Meropenem are β-lactam antibiotics that have a broad spectrum of antibacterial activity and are in addition good β-lactamase inhibitors. However they do not have good activity against MRSA.

It has now been found that a combination of vinyl-pyrrolidinone cephalosporins of the formula I with carbapenems also leads to a synergistic effect.

Compared to known combinations of two β-lactam antibiotics as described in the European Patent EP-A-384410, Banyu Pharmaceutical Co. Ltd; and compared to a combination of cephalosporins such as e.g. ceftriaxone and meropenem as described in the Japanese Laid Open Patent Publication JP-02-279627 A, Sumitomo, the combinations of the present invention show a higher efficacy against MRSA.

Furthermore, the combination comprises a unique broad spectrum of antibacterial activity that includes Gram-positive pathogens like, e.g. methicillin-sensitive and methicillin-resistant staphylococci, enterococci, penicillin-sensitive and penicillin-resistant pneumococci and Gram negative pathogens like, e.g. *E. coli, E. cloacae, K. pneumoniae, P. vulgaris, S. marcescens, C. freundii* and *P. aeruginosa*.

SUMMARY OF THE INVENTION

Accordingly, the present invention provides an antimicrobial composition comprising a combination of
(1) a therapeutically effective amount of a compound of formula I

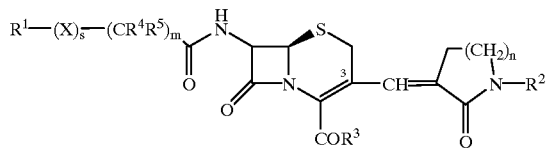

wherein
$R^1$ is lower alkyl, halogen, phenyl, benzyl, styryl, naphthyl or heterocyclyl; the lower alkyl, phenyl, benzyl, styryl, naphthyl and heterocyclyl being unsubstituted or substituted by one or more of the groups selected from halogen,
hydroxy,
amino,
lower alkylamino,
di-lower alkylamino,
carboxy,
lower alkylcarboxy,
carbamoyl,
lower alkylcarbamoyl,
unsubstituted lower alkyl or lower alkyl substituted by one or more groups selected from halogen, amino, hydroxy, cyano, carboxy, and carbamoyl,
unsubstituted lower alkoxy or lower alkoxy substituted by one or more groups selected from halogen, amino, hydroxy, cyano, carboxy, and carbamoyl,
unsubstituted phenyl or phenyl mono or di-substituted by halogen, unsubstituted lower alkyl or lower alkyl substituted by one or more groups selected from halogen, amino, hydroxy, cyano, carboxy, and carbamoyl, hydroxy or hydroxy protected with t-butyloxycarbonyl, trimethylsilyl, t-butyl-dimethylsilyl, tetrahydropyranyl, trifluoroacetyl, phosphate or sulfonate,
amino,
nitro or
trifluoromethyl;
$R^4$, $R^5$ are each independently hydrogen, lower alkyl or phenyl,
X is S, O, NH or $CH_2$;
n is 0, 1 or 2;
m is 0 or 1;
s is 0 or 1;
$R^2$ is hydrogen, hydroxy, carbamoylmethyl, $-CH_2-CO-NH-R^6$, lower alkyl-Qr, cycloalkyl-Qr, lower alkoxy, lower alkenyl, cycloalkenyl-Qr, lower alkynyl, aralkyl-Qr, aryl-Qr, aryloxy, aralkoxy, heterocyclyl or heterocyclyl-Qr; the lower alkyl-, cycloalkyl-, lower alkoxy-, lower alkenyl-, cycloalkenyl-, lower alkynyl-, aralkyl-, aryl-, aryloxy-, aralkoxy- and the heterocyclyl-group being unsubstituted or substituted with one or more groups selected from carboxy, amino, nitro, cyano, $-SO_2-NH-R^6$, unsubstituted lower alkyl or lower alkyl substituted by fluoro, lower alkoxy, hydroxy, halogen, $-CONR^6R^7$, $-CH_2-CONR^6R^7$, $N(R^7)COOR^8$, $R^7CO-$, $R^7OCO-$, $R^7COO-$, $-C(R^7R^9)CO_2R^8$, $-C(R^7R^9)CONR^7R^{10}$, wherein
$R^6$ is hydrogen, lower alkyl, cycloalkyl or aryl;
$R^7$ and $R^9$ are each independently hydrogen or lower alkyl;
$R^8$ is hydrogen, lower alkyl, lower alkenyl or a carboxylic acid protecting group; and
$R^{10}$ is hydrogen, co-hydroxy-alkyl, phenyl, naphthyl or heterocyclyl; the phenyl, naphthyl or heterocyclyl being unsubstituted or substituted with one or more groups selected from halogen, ω-hydroxyalkyl, cyano, unsubstituted lower alkyl or lower alkyl substituted by one or more groups selected from halogen, amino, hydroxy, cyano, carboxy, and carbamoyl, hydroxy or hydroxy protected with t-butyloxycarbonyl, trimethylsilyl, t-butyl-dimethylsilyl, tetrahydropyranyl, trifluoroacetyl, phosphate or sulfonate unsubstituted lower alkoxy or lower alkoxy substituted by one or more groups selected from halogen, amino, hydroxy, cyano, carboxy, and carbamoyl;

or $R^7$ and $R^{10}$ form together a group of formula

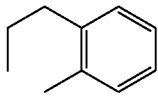

Q is —$CH_2$—, —CH-lower-alkyl, —CO— or —$SO_2$—;

r is 0 or 1; and $R^3$ is hydroxy, —O—, lower alkoxy, or —OM and M represents an alkali metal;

as well as readily hydrolyzable esters thereof, pharmaceutically acceptable salts of said compounds and hydrates of the compounds of formula I and of their esters and salts; and (2) a therapeutically effective amount of a second ingredient selected from the class of carbapenem antibiotics and pharmaceutically acceptable salts thereof or from β-lactamase inhibitors and pharmaceutically acceptable salts thereof; and a therapeutically inert carrier.

DETAILED DESCRIPTION OF THE INVENTION

The present invention provides an antimicrobial composition comprising a combination of (1) a therapeutically effective amount of a compound of formula I

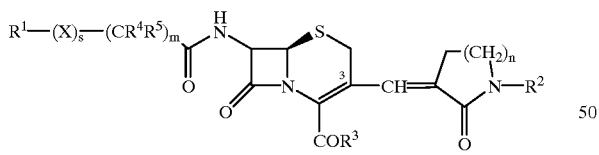

wherein $R^1$ is lower alkyl, halogen, phenyl, benzyl, styryl, naphthyl or heterocyclyl; the lower alkyl, phenyl, benzyl, styryl, naphthyl and heterocyclyl being unsubstituted or substituted by one or more of the groups selected from halogen, hydroxy, amino, lower alkylamino, di-lower alkylamino, carboxy, lower alkylcarboxy, carbamoyl, lower alkylcarbamoyl, unsubstituted lower alkyl or lower alkyl substituted by one or more groups selected from halogen, amino, hydroxy, cyano, carboxy, and carbamoyl, unsubstituted lower alkoxy or lower alkoxy substituted by one or more groups selected from halogen, amino, hydroxy, cyano, carboxy, and carbamoyl, unsubstituted phenyl or phenyl mono or di-substituted by halogen, unsubstituted lower alkyl or lower alkyl substituted by one or more groups selected from halogen, amino, hydroxy, cyano, carboxy, and carbamoyl, hydroxy or hydroxy protected with t-butyloxycarbonyl, trimethylsilyl, t-butyl-dimethylsilyl, tetrahydropyranyl, trifluoroacetyl, phosphate or sulfonate, amino, nitro or trifluoromethyl;

$R^4$, $R^5$ are each independently hydrogen, lower alkyl or phenyl;

X is Si O, NH or $CH_2$;

n is 0, 1 or 2;

m is 0 or 1;

s is 0 or 1;

$R^2$ is hydrogen, hydroxy, carbamoylmethyl, —$CH_2$—CO—NH—$R^6$, lower alkyl-Qr, cycloalkyl-Qr, lower alkoxy, lower alkenyl, cycloalkenyl-Qr, lower alkynyl, aralkyl-Qr, aryl-Qr, aryloxy, aralkoxy, heterocyclyl or heterocyclyl-Qr; the lower alkyl-, cycloalkyl-, lower alkoxy-, lower alkenyl-, cycloalkenyl-, lower alkynyl-, aralkyl-, aryl-, aryloxy-, aralkoxy- and the heterocyclyl-group being unsubstituted or substituted with one or more groups selected from carboxy, amino, nitro, cyano, —$SO_2$— NH—$R^6$, unsubstituted lower alkyl or lower alkyl substituted by fluoro, lower alkoxy, hydroxy, halogen, —$CONR^6R^7$, —$CH_2$—$CONR^6R^7$, N($R^7$) $COOR^8$, $R^7CO$—, $R^7OCO$—, $R^7COO$—, —C($R^7R^9$) $CO_2R^8$, —C($R^7R^9$)$CONR^7R^{10}$, wherein $R^6$ is hydrogen, lower alkyl, cycloalkyl or aryl;

$R^7$ and $R^9$ are each independently hydrogen or lower alkyl;

$R^8$ is hydrogen, lower alkyl, lower alkenyl or a carboxylic acid protecting group; and $R^{10}$ is hydrogen, (o-hydroxy-alkyl, phenyl, naphthyl or heterocyclyl; the phenyl, naphthyl or heterocyclyl being unsubstituted or substituted with one or more groups selected from halogen, ω-hydroxyalkyl, cyano, unsubstituted lower alkyl or lower alkyl substituted by one or more groups selected from halogen, amino, hydroxy, cyano, carboxy, and carbamoyl, hydroxy or hydroxy protected with t-butyloxycarbonyl, trimethylsilyl, t-butyl-dimethylsilyl, tetrahydropyranyl, trifluoroacetyl, phosphate or sulfonate unsubstituted lower alkoxy or lower alkoxy substituted by one or more groups selected from halogen, amino, hydroxy, cyano, carboxy, and carbamoyl;

or $R^7$ and $R^{10}$ form together a group of formula

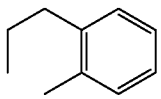

Q is —$CH_2$—, —CH-lower-alkyl, —CO— or —$SO_2$—;
r is 0 or 1; and
$R^3$ is hydroxy, —O—, lower alkoxy, or —OM and M represents an alkali metal;
as well as readily hydrolyzable esters thereof, pharmaceutically acceptable salts of said compounds and hydrates of the compounds of formula I and of their esters and salts; and (2) a therapeutically effective amount of a second ingredient selected from the class of carbapenem antibiotics and pharmaceutically acceptable salts thereof or from β-lactamase inhibitors and pharmaceutically acceptable salts thereof; and a therapeutically inert carrier.

The term "carbapenem antibiotics" denotes compounds containing the structural element

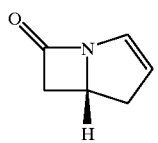

and exerting an antibiotic activity, such as e.g. imipenem or meropenem. Imipenem is preferred.

Preferred "β-lactamase inhibitors" are tazobactam, sulbactam, clavulanic acid or 3-β-alkenyl-penam-sulfon compounds as described in the European Patent EP-0 640 607 B1, particularly (Z)-(2S,3S,5R)-3-(2-cyanoethenyl)-3-methyl-4,4,7-trioxo-4-thia-1-aza-bicyclo[3.2.0]heptane-2-carboxylic acid and pharmaceutically acceptable salts having the following formula

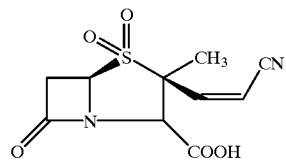

The compositions of the present invention are effective against MRSA which are highly resistant to β-lactam antibiotics and furthermore, provide a synergistic effect as compared to the compounds used alone.

As used herein pharmaceutically acceptable salts useful in this invention include salts derived from metals, the ammonium salt, quaternary ammonium salts derived from organic bases, amines and amino acid salts. Examples of preferred metal salts are those derived from the alkali metals, for example, lithium ($Li^+$), sodium ($Na^+$) and potassium ($K^+$). Examples of quaternary ammonium salts derived from organic bases include tetramethylammonium ($N^+(CH_3)_4$), tetraethylammonium ($N^+(CH_2CH_3)_4$), benzyltrimethylammonium ($N^+(C_6H_5CH_2)(CH_3)_3$), phenyltriethylammonium ($N^+(C_6H_5)(CeH_2CH_3)_3$), and the like, etc. Those salts derived from amines include salts with N-ethylpiperidine, procaine, lidocaine, dibenzylamine, N,N'-dibenzylethylenediamine, alkylamines or dialkylamines as well as salts with amino acids such as, for example, salts with arginine or lysine. With respect to vinyl-pyrrolidinone derivatives having basic or quaternary substituents $R^2$, also salts with mineral or organic acids are included. Especially preferred are hydrochlorides, sulfates, phosphates, lactates, mesylates or the inner salt.

As readily hydrolyzable esters of the compounds of formula I there are to be understood compounds of formula I, the carboxy group(s) of which (for example, the 2-carboxy group) is/are present in the form of readily hydrolyzable ester groups. Examples of such esters, which can be of the conventional type, are the lower alkanoyloxy-alkyl esters (e.g., the acetoxymethyl, pivaloyloxymethyl, 1-acetoxyethyl and 1-pivaloyloxyethyl ester), the lower alkoxycarbonyloxyalkyl esters (e.g., the methoxycarbonyl-oxymethyl, 1-ethoxycarbonyloxyethyl and 1-isopropoxycarbonyloxyethyl ester), the lactonyl esters (e.g., the phthalidyl and thiophthalidyl ester), the lower alkoxymethyl esters (e.g., the methoxymethyl ester) and the lower alkanoylaminomethyl esters (e.g., the acetamidomethyl ester). Other esters (e.g., the benzyl and cyanomethyl esters) can also be used. Other examples of such esters are the following: (2,2-dimethyl-1-oxopropoxy)methyl ester; 2-[(2-methyl propoxy)carbonyl]-2-pentenyl ester; 1-[[(1-methylethoxy)carbonyl]oxy] ethyl ester; 1-(acetyloxy) ethyl ester; (5-methyl-2-oxo-1,3-dioxol-4-yl) methyl ester; 1-[[(cyclohexyloxy)carbonyl]oxy] ethyl ester; and 3,3-dimethyl-2-oxobutyl ester. It will be appreciated by those of ordinary skill in the art that the readily hydrolyzable esters of the compounds of the present invention can be formed at a free carboxy group of the compound.

The compounds of formula I as well as their salts and readily hydrolyzable esters can be hydrated. The hydration can be effected in the course of making the compounds of formula I or can occur gradually as a result of hygroscopic properties of an initially anhydrous product.

Examples of salts of the compounds of formula I are defined under "pharmaceutically acceptable salts" above.

In above compounds of formula I the substituent in position 3 can be present in the E-form [Ia] or in the Z-form [Ib].

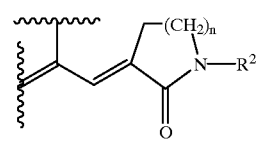

Ia

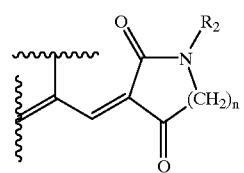

Ib

Compounds of formula Ia i.e. wherein the substituent in position 3 is in the E-form are generally preferred.

In a particular embodiment of the compounds of formula I n is 1.

The term "halogen" or "halo" used herein refers to all four forms, that is chlorine or chloro; bromine or bromo; iodine or iodo; and fluorine or fluoro, unless specified otherwise.

As used herein, the terms "alkyl" and "lower alkyl" refer to both straight and branched chain saturated hydrocarbon groups having 1 to 8, and preferably 1 to 4, carbon atoms, for example, methyl, ethyl, n-propyl, isopropyl, t-butyl and the like. In addition, the lower alkyl moiety can be substituted by one or more groups selected from for example, halogen, amino, hydroxy, cyano, carboxy, carbamoyl, etc., such as carboxymethyl, 2-fluoroacetyl, trifluoromethyl, 2,2,2-trifluoroethyl, 2-chloroethyl, hydroxymethyl, 2-hydroxyethyl, carbamoylmethyl and like.

As used herein, the term "lower alkoxy" refers to a straight or branched chain hydrocarbonoxy group wherein the "alkyl" portion is a lower alkyl group as defined above. Examples include methoxy, ethoxy, n-propoxy and the like. The "alkyl" portion may be substituted as defined above for lower alkyl.

As used herein, "alkenyl" and "lower alkenyl" refer to unsubstituted or substituted hydrocarbon chain radical having from 2 to 8 carbon atoms, preferably from 2 to 4 carbon atoms, and having at least one olefinic double bond, e.g. allyl, vinyl etc.

As used herein, "lower alkynyl" refers to unsubstituted or substituted hydrocarbon chain radical having from 2 to 8 carbon atoms, preferably 2 to 4 carbon atoms, and having at least one triple bond.

By the term "cycloalkyl" is meant a 3–7 membered saturated carbocyclic moiety, e.g., cyclopropyl, cyclobutyl, cyclohexyl, etc.

As used herein, "cycloalkenyl" refers to a carbocyclic ring radical having at least one olefinic double bond.

By the term "aryl" is meant a radical derived from an aromatic hydrocarbon by the elimination of one atom of hydrogen and can be substituted or unsubstituted. The aromatic hydrocarbon can be mononuclear or polynuclear. Examples of aryl of the mononuclear type include phenyl, tolyl, xylyl, mesityl, cumenyl, and the like. Examples of aryl of the polynuclear type include naphthyl, anthranyl, phenanthryl, and the like. The aryl group can have one or more substituents selected from, as for example, halogen, hydroxy, cyano, carboxy, nitro, amino, lower alkyl, lower alkoxy, carbamoyl, sulfamoyl; such as in 2,4-difluorophenyl, 4-carboxyphenyl, 4-nitrophenyl, 4-aminophenyl, 4-methoxyphenyl, 3-hydroxyphenyl, 4-hydroxyphenyl, 3-fluor-4-hydroxyphenyl, 4-sulfamoylbenzyl. When aryl is phenyl, it can be preferably mono or di-substituted by halogen, lower alkyl which is unsubstituted or substituted as above, optionally protected hydroxy or amino, nitro or trifluoromethyl.

By the term "aralkyl" is meant an alkyl group containing an aryl group. It is a hydrocarbon group having both aromatic and aliphatic structures, that is, a hydrocarbon group in which a lower alkyl hydrogen atom is substituted by a monocyclic aryl group, e.g., phenyl, tolyl, etc. Such groups are e.g. benzyl-groups.

As used herein, "aryloxy" is an oxygen radical having an aryl substituent (i.e., -O-aryl).

As used herein, "aralkoxy" is an oxygen radical having an aralkyl substituent.

As used herein, the term "lower alkylamino and di-lower alkylamino" refers to mono and dialkylamino residues wherein lower alkyl is as defined above, for example methylamino, 2-ethylamino, —CH$_2$NHCH$_3$, —CH$_2$CH$_2$NHCH$_3$, —CH$_2$CH$_2$N(CH$_3$)$_2$, N-methylamino, N-ethylamino, N,N-dimethylamino, N,N-diethylamino and the like.

As used herein, "heterocyclic ring" or "heterocyclyl"refers to an unsaturated or saturated, unsubstituted or substituted, mono or bicyclic 4-, 5-, 6-, or 7-membered heterocyclic ring containing one or more hetero atoms selected from the group consisting of oxygen, nitrogen, or sulfur. Exemplary heterocyclic rings include, but are not limited to, for example, the following groups: azetidinyl, pyridyl, pyrazinyl, piperidyl, piperidino, N-oxido-pyridyl, pyrimidyl, piperazinyl, pyrrolidinyl, pyridazinyl, N-oxide-pyridazinyl, pyrazolyl, triazinyl, imidazolyl, thiazolyl, quinoline, benzothiazolyl, benzoxazolyl, benzimidazolyl, 1,2,3-thiadiazolyl, 1,2,4-thiadiazolyl, 1,3,4-thiadiazolyl, 1,2,3-oxadiazolyl, 1,2,4-oxadiazolyl, 1,3,4-oxadiazolyl, 1,2,3-triazolyl, 1,2,4-triazolyl, 1H-tetrazolyl, 2H-tetrazolyl; furyl, 1H-azepinyl, thiophenyl, tetrahydrothiophenyl, tetrahydrofuranyl, isoxazolyl, isothiazolyl, oxazolidinyl, 1H-pyrazolo [3,4-d]pyrimidin-4-yl, [1,2,4] triazolo [1,5-a] pyrimidin-7-yl, 5-oxo-2,5-dihydro-[1,2,4] triazin-3-yl, 2-oxo-3,7-dihydro-2H-purin-6-yl, etc. Substituents for the heterocyclic ring include, for example, lower alkyls such as methyl, ethyl, propyl, etc., lower alkoxys such as methoxy, ethoxy, etc., halogens such as fluorine, chlorine, bromine, etc., halogen substituted alkyls such as trifluoromethyl, trichloroethyl, etc., amino, mercapto, hydroxyl, carbamoyl, or carboxyl groups. A further substituent is oxo, such as in 2-oxo-oxazolidin-3-yl, 1,1-dioxo-tetrahydrothiophen-3-yl. Further examples of substituted heterocycles are 6-methoxy-pyridin-3-yl, 5-methyl-isoxazol-3-yl, 1-methyl-pyridinium-2-yl, -3-yl, -4-yl, 1-carbamoylmethyl-pyridinium-2-yl, 1-carbamoylmethyl-pyridinium-3-yl, 1-carbamoylmethyl-pyridinium-2-yl, -3-yl, -4-yl, 1-[N-(4-hydroxy)phenyl]-carbamoylmethyl-pyridinium-4-yl, 1-[N-(3-fluoro-4-hydroxy)phenyl]-carbamoylmethyl-pyridinium-4-yl.

The term "optionally protected hydroxy" refers to hydroxy or hydroxy protected, for example with t-butyloxycarbonyl, trimethylsilyl, t-butyl-dimethylsilyl, tetrahydropyranyl, trifluoroacetyl, and the like, or refers to an ester group, for example, phosphate or sulfonate.

The term "optionally protected amino" refers to amino or amino protected with, for example, BOC [t-butoxycarbonyl; other name: (1,1-dimethylethoxy)carbonyl], benzyloxycarbonyl and allyloxycarbonyl.

The term "carboxylic acid protecting group" refers to protecting groups conventionally used to replace the acidic proton of a carboxylic acid.

Examples of such groups are described in Greene, T., Protective Groups in Organic Synthesis, Chapter 5, pp. 152–192 (John Wiley and Sons, Inc. 1981), incorporated herein by reference. Preferably these examples include methoxymethyl, methylthiomethyl, 2,2,2-trichloroethyl, 2-haloethyl, 2-(trimethylsilyl)ethyl, t-butyl, allyl, benzyl, triphenylmethyl (trityl), benzhydryl, p-nitrobenzyl, p-methoxybenzyl, trimethylsilyl, triethylsilyl, t-butyldimethylsilyl, i-propyl-dimethylsilyl. Preferred are benzyhydryl, t-butyl, p-nitrobenzyl, p-methoxybenzyl and allyl.

A preferred embodiment of the invention are compounds of formula I wherein $R^1$ is phenyl, 3,4-dichlorophenyl, 2,5-dichlorophenyl, 3,5-dichlorophenyl, 2,4,5-trichlorophenyl, 4-trifluoromethyl-phenyl, 4-methoxyphenyl, 4-hydroxymethylphenyl, 3,4-dimethoxyphenyl, 2-naphthyl, benzyl, 2-benzothiazolyl, 2-benzoxazolyl, 4-methyl-1,2,4-triazol-5-yl, 1-methyl-tetrazol-5-yl, benzimidazol-2-yl, (2-amino)-thiazol-4-yl, pyridin-4-yl, pyrimidin-2-yl, pyridinium-1-yl, 2-yl, -3-yl or -4-yl;

$R^2$ is cyclopropyl, cyclopropylmethyl, 1,1,1-trifluorethyl, 2,-3- or 4-hydroxybenzyl, 4-hydroxyphenyl, 4-sulfamoylbenzyl, pyrrolidin-3-yl or a group of formula

9

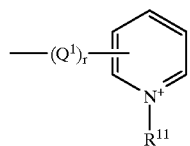

wherein
$Q^1$ is —$CH_2$—
r is 0 or 1;
$R^{11}$ is hydrogen, lower alkyl, (o-hydroxy alkyl, benzyl or alkyl-heterocyclyl;
  the benzyl and the heterocyclyl group being unsubstituted or substituted with one or more groups selected from cyano, carboxy or hydroxy; or is —$CH_2CONR^7R^{10}$; wherein $R^7$ and $R^{10}$ are as defined above.
$R^3$ is hydroxy, —O—, or —OM and M represents an alkali metal;
X is S;
$(CR^4R^5)_m$ is —$CH_2$—;
s is 1;
and pharmaceutically acceptable salts thereof.
An especially preferred embodiment of the invention are compounds of formula I wherein $R^1$ is phenyl, 2-naphthyl, 2,5-dichlorophenyl, 3,5-dichlorophenyl, 2,4,5-trichlorophenyl, 2-benzothiazolyl, 4-pyridinyl;

10

$R^2$ is cyclopropyl, methyl-cyclopropyl, 3- or 4-hydroxybenzyl, 4-hydroxyphenyl, 4-sulfamoylbenzyl, pyrrolidin-3-yl, 1-[N-(4-hydroxy)phenyl]-carbamoylmethyl-pyridin-1-ium-4-yl, 1-[N-(3-fluoro-4-hydroxy)phenyl]-carbamoylmethyl-pyridin-1-ium-4-yl.
$R^3$ is hydroxy, —O—, lower-alkoxy, or —OM and M represents an alkali metal;
X is S;
$(CR^4R^5)_m$ is —$CH_2$—;
s is 1;
and pharmaceutically acceptable salts thereof.

Especially preferred compounds of formula I are: (E)-(6R,7R)-3-[1-[1-[(4-Hydroxy-phenylcarbamoyl)-methyl]-pyridin-1-ium-4-ylmethyl]-2-oxo-pyrrolidin-3-ylidenemethyl]-8-oxo-7-[2-(2,4,5-trichloro-phenylsulfanyl)-acetylamino]-5-thia-1-aza-bicyclo[4.2.0]oct-2-ene-2-carboxylate (Example 1),

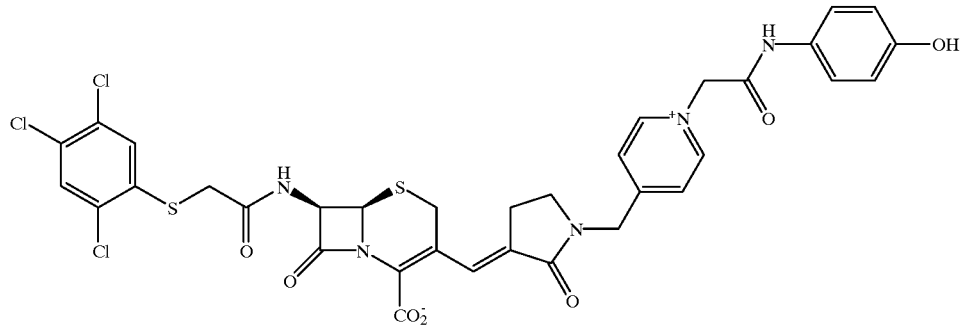

(E)-(6R,7R)-3-[1-[1-[(4-Hydroxy-phenylcarbamoyl)-methyl]-pyridin-1-ium-4-ylmethyl]-2-oxo-pyrrolidin-3-ylidenemethyl]-8-oxo-7-[2-(1-benzothiazol-2-ylsulfanyl)-acetylamino]-5-thia-1-aza-bicyclo[4.2.0]oct-2-ene-2-carboxylate (Example 2),

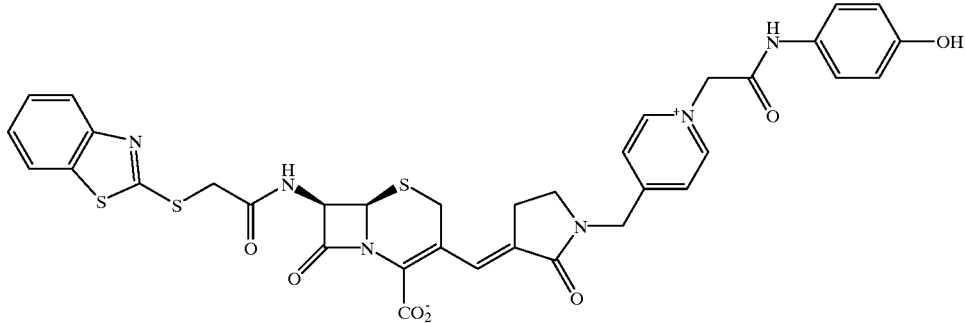

(E)-(6R,7R)-7-[2-(Benzothiazol-2-ylsulfanyl)-acetylamino]-3-(1-cyclopropyl-methyl-2-oxo-pyrrolidin-3-ylidenemethyl)-8-oxo-5-thia-1-aza-bicyclo[4.2.0]oct-2-ene-2-carboxylic acid (Example 3),

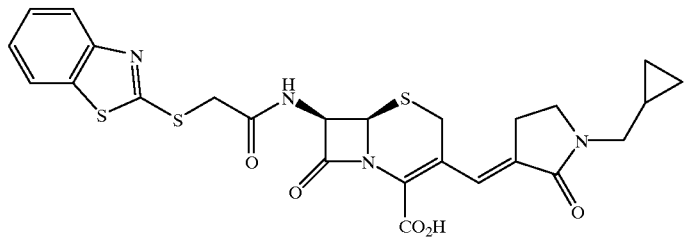

(E)-(6R,7R)-3-[1-[1-[(4-Hydroxy-phenylcarbamoyl)-methyl]-pyridin-1-ium-4-ylmethyl]-2-oxo-pyrrolidin-3-ylidenemethyl]-8-oxo-7-[2-(pyridin-4-ylsulfanyl)-acetylamino]-5-thia-1-aza-bicyclo[4.2.01]oct-2-ene-2-carboxylate (Example 4),

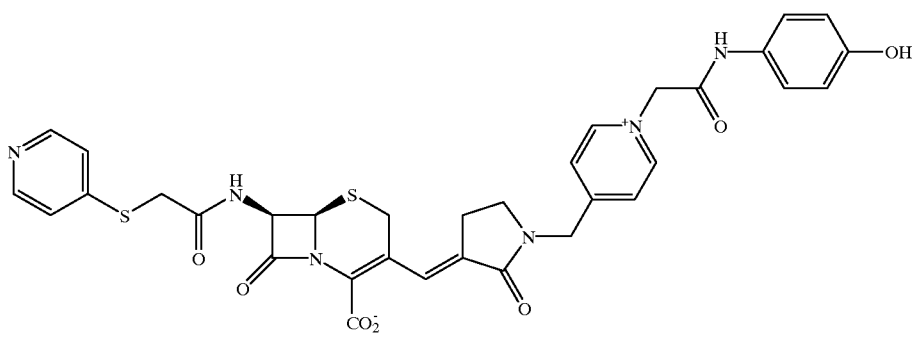

(E)-(6R,7R)-3-[1-[1-[(3-Fluoro-4-hydroxy-phenylcarbamoyl)-methyl]-pyridin-1-ium-4-ylmethyl]-2-oxo-pyrrolidin-3-ylidenemethyl]-7-[2-(naphthalen-2-ylsulfanyl)-acetyl amino]-8-oxo-5-thia-1-aza-bicyclo[4.2.0]oct-2-ene-2-carboxylate (Example 5),

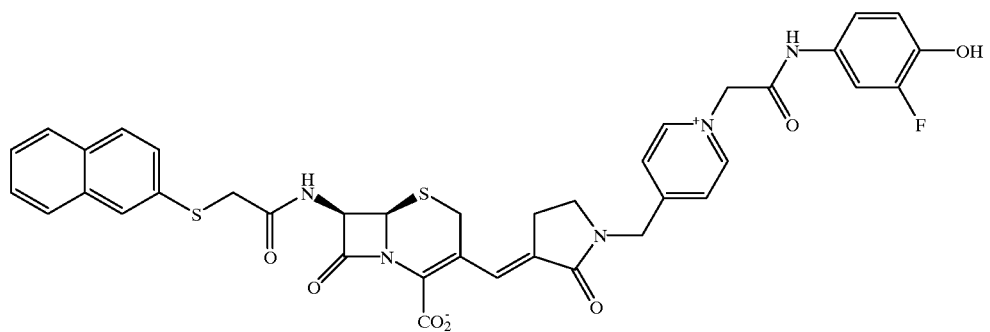

(E)-(6R,7R)-3-[1-(3-Hydroxy-benzyl)-2-oxo-pyrrolidin-3-ylidenemethyl]-8-oxo-7-[2-(2,4,5-trichloro-phenylsulfanyl)-acetylamino]-5-thia-1-aza-bicyclo[4.2.0]oct-2-ene-2-carboxylic acid (Example 6),

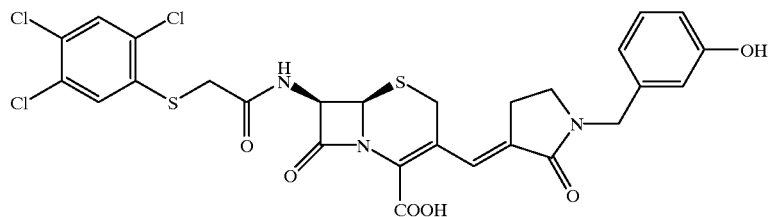

(E)-(6R,7S)-3-[1-(3-Hydroxy-benzyl)-2-oxo-pyrrolidin-3-ylidenemethyl]-8-oxo-7-[2-naphthalen-2-ylsulfanyl)-acetylamino]-5-thia-1-aza-bicyclo[4.2.0]oct-2-ene-2-carboxylic acid (Example 7),

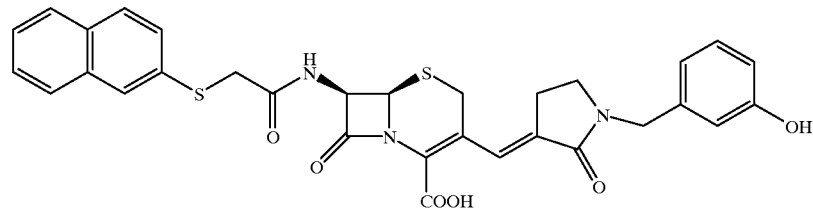

Mixture of (E)-(6R,7R)-3-[(R)- and -[(S)-2-oxo-[1,3']Bipyrrolidinyl-3-ylidene-methyl]-8-oxo-7-[2-(2,4,5-trichloro-phenylsulfanyl)-acetylamino]-5-thia-1-aza-bicyclo[4.2.0]oct-2-ene-2-carboxylic acid hydrochloride (Example 8),

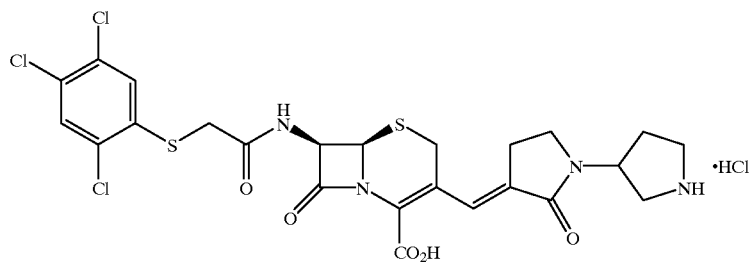

(E)-(6R,7R)-3-[1-[1-[(3-Fluoro-4-hydroxy-phenylcarbamoyl)-methyl]-pyridin-1-ium-4-ylmethyl]-2-oxo-pyrrolidin-3-ylidenemethyl]-8-oxo-7-(2-phenylsulfanyl-acetylamino)-5-thia-1-aza-bicyclo[4.2.0]oct-2-ene-2-carboxylate (Example 9)

(E)-(6R,7R)-7-[2-(2,5-Dichloro-phenylsulfanyl)-acetylamino]-3-[1-[(3-fluoro-4-hydroxy-phenylcarbamoyl)-methyl]-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate (Example 10),

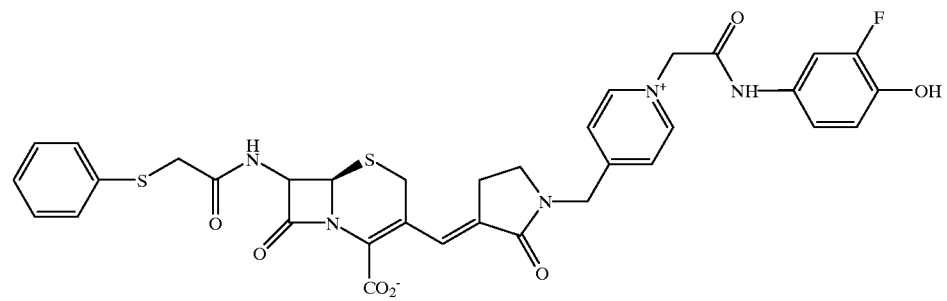

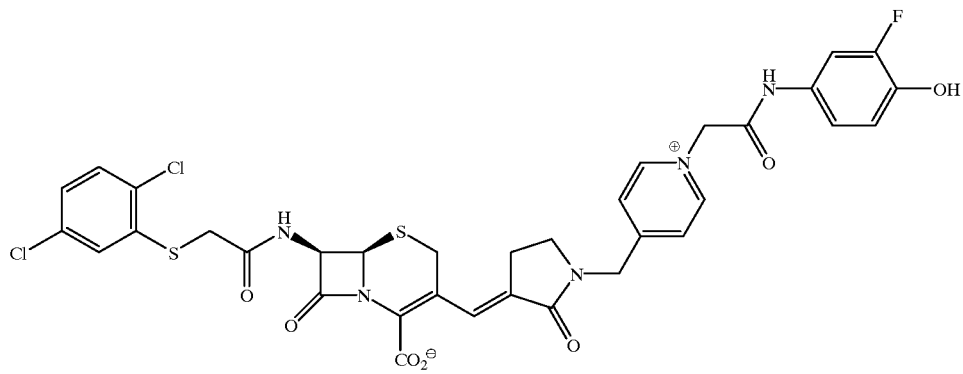

(E)-(6R,7R)-8-oxo-3-[(R)-2-oxo-[1,3']Bipyrrolidinyl-3-ylidenemethyl]-7-[2-(phenylsulfanyl)-acetylamino]-5-thia-1-aza-bicyclo[4.2.0]oct-2-ene-2-carboxylic acid hydrochloride (Example 11), (E)-(6R,7R)-8-Oxo-3-[2-oxo-1-(4-sulfamoyl-benzyl)-pyrrolidin-3-ylidenemethyl]-7-[2-phenylsulfanyl)-acetylamino]-5-thia-1-aza-bicyclo[4.2.0]oct-2-ene-2-carboxylic acid (Example 14).

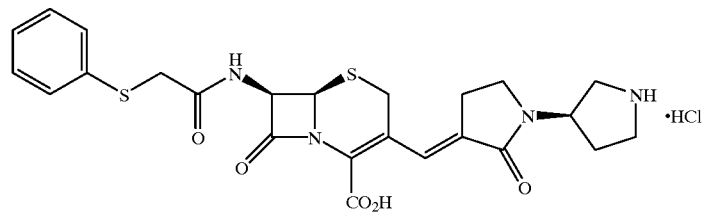

(E)-(6R,7R)-3-(1-Cyclopropyl-2-oxo-pyrrolidin-3-ylidenemethyl)-7-[2-(naphthalene-2-ylsulfanyl)-acetylamino]-8-oxo-5-thia-1-aza-bicyclo[4.2.0]oct-2-ene-2-carboxylic acid (Example 12),

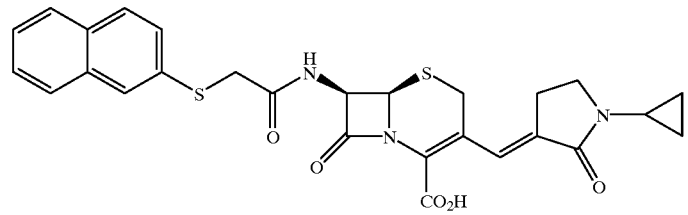

(E)-(6R,7R)-3-[1-(4-Hydroxy-phenyl)-2-oxo-pyrrolidin-3-ylidenemethyl]-7-[2-(naphthalene-2-ylsulfanyl)-acetylamino]-8-oxo-5-thia-1-aza-bicyclo[4.2.0]oct-2-ene-2-carboxylic acid sodium salt (1:1) (Example 13),

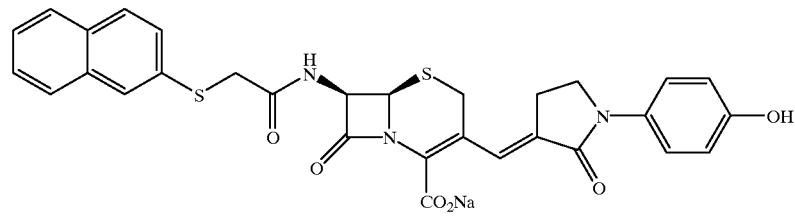

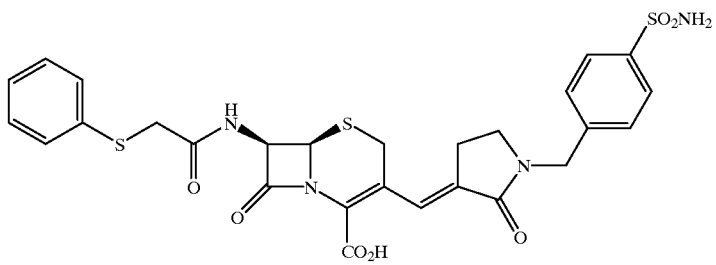

In one aspect of the invention the first ingredient and the second ingredient as defined above are formulated in a single composition, and in another embodiment, the first and the second ingredient are separately formulated in different compositions. Thus, the invention also comprises a kit consisting of a composition containing a compound of formula I in dosage unit form and a second composition in dosage unit form containing a carbapenem antibiotic or a β-lactamase inhibitor as defined earlier.

The ratio of the compound of (1) to the second ingredient of (2) can be widely varied, and is usually about 1:20 to about 20:1.

The present composition can be administered in the same manner as the ingredients alone, i.e., can be administered parenterally, orally or topically. For parenteral administration the compositions are preferably made into preparations as lyophilisates or dry powders for dilution with customary agents, such as water, isotonic common salt solution or carbohydrate.

Where the composition comprising both the first and the second ingredient is administered the total amount administered is from about 0.25 to about 8 g/day.

The synergism of the present composition is demonstrated by testing representative compounds of the present invention. In vitro activity was determined by minimum inhibitory concentration (MIC) by the agar dilution method in Mueller Hinton agar inoculum $=10^5$ CFU/spot.

Table 1 shows the in vitro activity (MIC, [mg/L]) of selected cephalosporins in combination with 4 mg/L Imipenem against 17 highly resistant MRSA strains.

TABLE 1

| Example | $MIC_{50}$ | $MIC_{90}$ | $MIC_{100}$ | range of MIC |
|---|---|---|---|---|
| Imipenem | >16 | >16 | >16 | 16–>16 |
| Meropenem | >16 | >16 | >16 | 16–>16 |
| Cefoperazone | >64 | >64 | >64 | >64 |
| Cefotiam | >64 | >64 | >64 | >64 |
| Cefpiramid | >64 | >64 | >64 | >64 |
| Ceftriaxone | >64 | >64 | >64 | >64 |
| Cefotaxime | >64 | >64 | >64 | >64 |
| Cefoperazone + Imipenem[1] | >64 | >64 | >64 | >64 |
| Cefotiam + Imipenem[1] | >64 | >64 | >64 | 64–>64 |
| Cefpiramid + Imipenem[1] | >64 | >64 | >64 | 32–>64 |
| Ceftriaxone + Imipenem | >64 | >64 | >64 | >64 |
| Cefotaxime + Imipenem | >64 | >64 | >64 | >64 |
| Ceftriaxone + Meropenem[2] | >64 | >64 | >64 | >64 |
| Cefotaxime + Meropenem[2] | >64 | >64 | >64 | >64 |
| Ex. 1 | >16 | >16 | >16 | 2–>16 |
| Ex. 1 + Imipenem | 0.5 | 1 | 2 | ≦0.12–2 |
| Ex. 2 | >16 | >16 | >16 | 2–>16 |
| Ex. 2 + Imipenem | 1 | 1 | 2 | 0.25–2 |
| Ex. 3 | 16 | >16 | >16 | 2–>16 |
| Ex. 3 + Imipenem | 2 | 4 | 4 | 1–4 |
| Ex. 4 | >16 | >16 | >16 | 4–>16 |
| Ex. 4 + Imipenem | 1 | 2 | 2 | 0.25–2 |

TABLE 1-continued

| Example | $MIC_{50}$ | $MIC_{90}$ | $MIC_{100}$ | range of MIC |
|---|---|---|---|---|
| Ex. 5 | >16 | >16 | >16 | 2–>16 |
| Ex. 5 + Imipenem | 0.5 | 2 | 2 | ≦0.12–2 |
| Ex. 6 | 16 | >16 | >16 | 1–>16 |
| Ex. 6 + Imipenem | 2 | 4 | 4 | ≦0.12–4 |
| Ex. 7 | 16 | 16 | 16 | 2–16 |
| Ex. 7 + Imipenem | 1 | 4 | 4 | 0.5–4 |
| Ex. 8 | >16 | >16 | >16 | 2–>16 |
| Ex. 8 + Imipenem | 0.5 | 2 | 4 | ≦0.12–4 |
| Ex. 9 | 16 | 16 | >16 | 1–>16 |
| Ex. 9 + Imipenem | 0.5 | 1 | 1 | ≦0.12–1 |
| Ex. 10 | >16 | >16 | >16 | 1–>16 |
| Ex. 10 + Imipenem | 0.5 | 1 | 2 | ≦0.12–2 |
| Ex. 11 | 16 | >16 | >16 | 4–>16 |
| Ex. 11 + Imipenem | 0.5 | 1 | 2 | ≦0.25–2 |
| Ex. 12 | 16 | >16 | >16 | 4–>16 |
| Ex. 12 + Imipenem | 2 | 4 | 4 | 0.5–4 |
| Ex. 13 | 16 | >16 | >16 | 2–>16 |
| Ex. 13 + Imipenem | 1 | 2 | 2 | ≦0.25–2 |
| Ex. 14 | 16 | >16 | >16 | 1–>16 |
| Ex. 14 + Imipenem | 1 | 4 | 8 | ≦0.25–8 |

1) combination described in EP-A 0 384 410
2) combination described in JP-02-279627 A Table 2 shows the in vitro activity (MIC, [mg/L]) of selected cephalosporins in combination with 4 mg/L compound B (sodium -(Z)-(2S,3S ,R)-3-(2-cyanoethenyl)-3-methyl-4,4,7-trioxo-4-thia-1-aza-bicyclo[3.2.0]heptane-2-carboxylate) of the formula

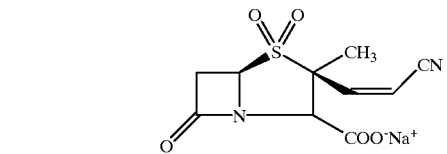

against 17 highly resistant MRSA strains

TABLE 2

| Example | $MIC_{50}$ | $MIC_{90}$ | $MIC_{100}$ | range of MIC |
|---|---|---|---|---|
| compound B | >16 | >16 | >16 | >16 |
| Ex. 1 | >16 | >16 | >16 | 2–>16 |
| Ex. 1 + compound B | 2 | 2 | 2 | 1–2 |
| Ex. 2 | >16 | >16 | >16 | 2–>16 |
| Ex. 2 + compound B | 2 | 2 | 4 | 2–4 |
| Ex. 4 | >16 | >16 | >16 | 4–>16 |
| Ex.4 + compound B | 4 | 8 | 8 | 4–8 |
| Ex. 5 | >16 | >16 | >16 | 2–>16 |
| Ex. 5 + compound B | 2 | 2 | 2 | 1–2 |
| Ex. 6 | 16 | >16 | >16 | 1–>16 |
| Ex. 6 + compound B | 2 | 2 | 4 | 1–4 |
| Ex. 7 | 16 | 16 | 16 | 2–16 |

TABLE 2-continued

| Example | MIC$_{50}$ | MIC$_{90}$ | MIC$_{100}$ | range of MIC |
|---|---|---|---|---|
| Ex. 7 + compound B | 2 | 4 | 4 | 2–4 |
| Ex. 8 | >16 | >16 | >16 | 2–>16 |
| Ex. 8 + compound B | 2 | 4 | 4 | 0.5–4 |
| Ex. 9 | 16 | 16 | >16 | 1–>16 |
| Ex. 9 + compound B | 2 | 2 | 2 | 0.5–2 |
| Ex. 10 | >16 | >16 | >16 | 1–>16 |
| Ex. 10 + compound B | 1 | 2 | 2 | 0.5–2 |
| Ex. 11 | 16 | >16 | >16 | 4–>16 |
| Ex. 11 + compound B | 2 | 2 | 4 | 1–4 |
| Ex. 12 | 16 | >16 | >16 | 4–>16 |
| Ex. 12 + compound B | 4 | 8 | 8 | 2–8 |

The compounds of the formula I as well as their pharmaceutical acceptable salts, hydrates, or readily hydrolyzable esters can be made by (a) treating a compound having the formula II

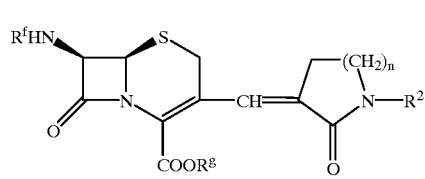

in which $R^2$ and n are defined above;

$R^f$ is hydrogen or trimethylsilyl; and $R^g$ is hydrogen, benzhydryl, p-methoxybenzyl, t-butyl, trimethylsilyl or allyl or salt thereof, with a carboxylic acid of the general formula III

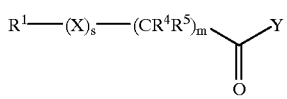

in which $R^1$, X, s, $R^4$, $R^5$ and m are as defined above, and

Y is —OH, or a reactive functional derivative thereof wherein Y is, for example a halogen as chloride or bromide, or 1-imidazolyl, 2-mercaptobenzotriazolyl, 1-hydroxy—benzotriazolyl or pivaloyloxy;

(b) for compounds of formula I wherein X is S, O or NH, by treating a compound having the formula IV

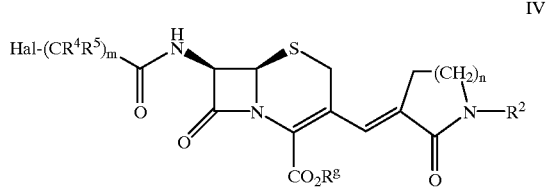

wherein $R^4$, $R^5$, m, n, $R^2$ and $R^g$ are as defined above and

Hal stands for halogen as bromine or chlorine or iodide preferably bromine, with an appropriate thiol or thiolate or an appropriate alcohol or alcoholate or an appropriate amine in the presence of a base, (c) for making the readily hydrolysable ester of a compound of formula I by subjecting a carboxylic acid of formula I to a corresponding esterification or (d) for making the salt or hydrates of a compound of formula I or hydrates of said salts by converting a compound of formula I into a salt or hydrate or into a hydrate of said salts.

The reaction of a compound of formula II prepared according to embodiment (a) with a compound of formula III, or a reactive derivative thereof can be carried out in a manner known per se. The carboxy groups in compounds of formula II (carboxy group in position 2 and/or carboxy groups optionally present in $R^2$) in compounds of formula III (carboxy groups optionally present in $R^1$) can be protected intermediatly or in situ, for example, by esterification to form readily cleavable esters such as a silyl ester (e.g. trimethylsilylester), a p-methoxy-benzylester or benzhydryl ester.

Furthermore the amino groups present in compounds of formula II (in position 7 and/or optionally present in $R^2$) and/or optionally present in $R^1$ of compounds of formula III can be protected, for example, with protecting groups which are cleavable by acid hydrolysis (e.g. the t-butoxy-carbonyl or triphenylmethyl groups), by basic hydrolysis (e.g. the trifluoroacetyl group), by hydrazinolysis (e.g. the phthalimido group) or by catalytic cleavage in presence of Pd (the allyloxycarbonyl group). Preferred protecting groups are the t-butyloxy-carbonyl, allyloxycarbonyl, the chloroacetyl, bromoacetyl and iodoacetyl groups, especially the chloroacetyl group. These last-mentioned protecting groups can be cleaved off by treatment with thiourea. Another preferred protecting group is phenylacetyl which can be cleaved off by treatment with $PCl_5$ or enzymatically.

The 7-amino group in compounds II can be protected in situ, for example, by a silyl protecting group such as the trimethylsilyl group.

In reacting a 7-amino compound of formula II with a carboxylic acid of formula III in the presence of an activating agent such as CDI (1,1'-carbonyl-diimidazole), CDT (1,1'-carbonyl-1,2,4-ditriazole), DCC (N,N'-dicyclohexylcarbodiimide), EEDQ (1-ethoxycarbonyl-2-ethoxy-1,2-dihydroquinoline), HOBT (1-Hydroxybenzotriazole), HBTU (ortho-benzotriazol-1-yl-N,N,N',N'-tetramethyluronium-hexafluorphosphate), isobutyl chlorocarbonate, IIDQ (1-isobutyloxycarbonyl-2-isobutyloxy-1,2-dihydroquinoline), pivaloyl chloride and the like or a reactive functional derivative of formula III, in an inert solvent such as ethyl acetate, acetonitrile, dioxane, chloroform, methylene chloride, benzene, dimethylformamide or dimethylacetamide can be used. Subsequently the ester group can be cleaved off.

Prepared according to another embodiment, a salt of an acid of formula II (e.g. a trialkylammonium salt such as the triethylammonium salt) is reacted with a reactive functional derivative of a carboxylic acid of formula III in an inert solvent (e.g. dimethylformamide, dimethylacetamide, dimethylsulfoxide and the like).

The reaction of a 7-amino compound of formula II with the carboxylic acid of formula III or a reactive derivative thereof can conveniently be carried out at a temperature between about $-40°$ C. and $+60°$ C., e.g. at room temperature.

Embodiment (b) involves treating a compound of formula IV with an appropriate thiol or thiolate or an appropriate alcohol or alcoholate or an appropriate amine in presence of a base, for example, trialkylamine such as trimethylamine, triethylamine, sodium bicarbonate, DBU (1,8-diazabicyclo

[5,4,0]undec-7-en(1,5-5)) to form the corresponding thioether, ether or amine. Optionally present amino, hydroxy or carboxyl groups can be intermediately protected with groups as described above.

Deprotection of protected amino, hydroxy or carboxylic groups present in a compound of formulae II, III and IV can be carried out as follows:

Removal of amino protecting groups

Possible amino-protecting groups are those employed in peptide chemistry, such as the protecting groups mentioned above. Preferably these examples include carbamates, e.g. fluorenylmethyl, 2,2,2-trichloroethyl, t-butyl, triphenylmethyl, allyl, benzyl. Further protecting groups are p-nitro-benzyl, diphenylmethyl, triphenylmethyl, benzyl, formyl, trifluoroacetyl, chloro-acetyl, the cyclic imides of N-phthaloyl, N-trimethylsilyl, N-benzenesulfonyl, N-toluenesulfonyl. Preferred is BOC [t-butoxycarbonyl; other name: (1,1-dimethylethoxy)carbonyl], benzyloxycarbonyl, allyloxy-carbonyl or trimethylsilyl.

The amino protecting groups may be cleaved off by acid hydrolysis (e.g. the t-butoxycarbonyl or triphenylmethyl group), e.g. aqueous formic acid, trifluoroacetic acid or by basic hydrolysis (e.g. the trifluoroacetyl group). The chloroacetyl, bromoacetyl and iodoacetyl groups are cleaved off by treatment with thiourea. The trimethylsilyl group is cleaved off by hydrolysis or alcoholysis.

Amino-protecting groups which are cleavable by acid hydrolysis are preferably removed with the aid of a lower alkanecarboxylic acid which may be halogenated. In particular, formic acid or trifluoroacetic acid is used. The reaction is carried out in the acid or in the presence of a co-solvent such as a halogenated lower alkane, e.g. methylene chloride. The acid hydrolysis is generally carried out at room temperature, although it can be carried out at a slightly higher or slightly lower temperature (e.g. a temperature in the range of about −30° C. to +40° C.). Protecting groups which are cleavable under basic conditions are generally hydrolyzed with dilute aqueous caustic alkali at 0° C. to 30° C. The chloroacetyl, bromoacetyl and iodoacetyl protecting groups can be cleaved off using thiourea in acidic, neutral or alkaline medium at about 0° C.–30° C. The phthalimido group can be cleaved off with hydrazine at −20° C. to +50° C.

Removal of hydroxy protecting groups

Possible hydroxy protecting groups are such as are commonly known in the art, such as trimethylsilyl, t-butyldimethylsilyl, dimethylphenylsilyl, triphenylmethyl, lower alkanoyl, acetyl, trifluoroacetyl, tetrahydropyranyl, benzyl, p-nitrobenzyl or t-butoxycarbonyl. These groups are removed in the presence of acidic solvents, weak organic acids or weak inorganic bases like sodium bicarbonate, respectively.

Removal of protecting groups at the carboxy function

As carboxyl protecting groups one may utilize an ester form which can be easily converted into a free carboxyl group under mild conditions, for example, benzhydryl, t-butyl, p-nitrobenzyl, p-methoxybenzyl, allyl, etc.

These protecting groups may be removed as follows:
benzhydryl trifluoroacetic acid with anisol, phenol, cresol or triethylsilane at about −40° C. to room temperature; hydrogen with Pd/C in an alcohol such as ethanol or in tetrahydrofuran; BF$_3$-etherate in acetic acid at about 0 to 50° C.;

t-butyl formic acid or trifluoroacetic acid with or without anisol, phenol, cresol or triethylsilane and a solvent such as dichloromethane at about -10° C. to room temperature;

p-nitrobenzyl sodium sulfide in acetone/water at about 0 to room temperature; or hydrogen with Pd/C in an alcohol such as ethanol or in tetrahydrofuran;

p-methoxybenzyl formic acid at about 0 to 50° C.; or trifluoroacetic acid and anisole, phenol or triethylsilane at about −40° C. to room temperature;

allyl palladium(O) catalyzed transalkylation reaction in the presence of sodium or potassium salt of 2-ethyl hexanoic acid, see for example J. Org. Chem. 1982, 47, 587.

trimethylsilyl by hydrolysis or alcoholysis at room temperature.

In order to make a readily hydrolysable ester of the carboxylic acids of formula I in accordance with embodiment (c) a carboxylic acid of formula I is preferably reacted with a corresponding halide, preferably an iodide, containing the desired ester group. The reaction can be accelerated with the aid of a base such as an alkali metal hydroxide, an alkali metal carbonate or an organic amine such as triethylamine. The esterification is preferably carried out in an inert organic solvent such as dimethyl-acetamide, hexamethylphosphoric acid triamide, dimethyl sulfoxide or, especially, dimethylformamide. The reaction is preferably carried out at a temperature in the range of about 0–40° C.

Making the salts and hydrates of the compounds of formula I or the hydrates of said salts in accordance with embodiment (d) can be carried out in a manner known per se; for example, by reacting a carboxylic acid of formula I or a salt thereof with an equivalent amount of the desired base, conveniently in a solvent such as water or an organic solvent (e.g. ethanol, methanol, acetone and the like). Correspondingly, salt formation is brought about by the addition of an organic or inorganic salt or an acid. The temperature at which the salt formation is carried out is not critical. The salt formation is generally carried out at room temperature, but it can be carried out at a temperature slightly above or below room temperature, for example in the range of 0° C. to +50° C.

Making the hydrates usually takes place automatically in the course of the process or as a result of the hygroscopic properties of an initially anhydrous product. For the controlled of a hydrate, a completely or partially anhydrous carboxylic acid of formula I or salt thereof can be exposed to a moist atmosphere (e.g. at about +10° C. to +40° C.).

Exemplary of the process for obtaining products in accordance with the invention are the following reaction schemes 1 and 2 below.

Scheme 1,
embodiment (a)

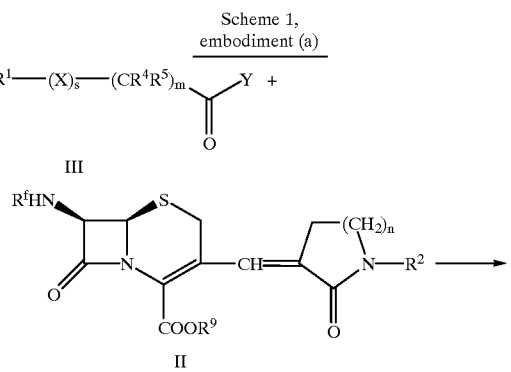

-continued

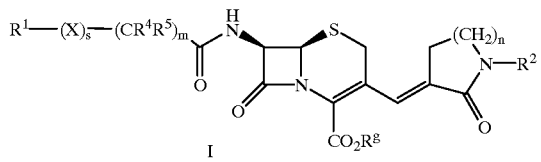

wherein the symbols are as defined above.

To a solution of 68.4 mg (0.25 mmol) (2,4,5-trichlorophenylsulfanyl)-acetic acid in 3 ml N,N-dimethylacetamide were added under stirring and Argon atmosphere 40.9 mg (0.25 mmol) 1,1'-carbonyldiimidazole. After 30 min, 136.4 mg (0.21 mmol) (E)-(6R,7R)-7-amino-3-[1-[1-[(4-hydroxyphenyl-carbamoyl)-methyl]-pyridin-1-ium-4-ylmethyl]-2-oxo-pyrrolidin-3-ylidene -methyl]-8-oxo-5-thia-1-aza-bicyclo[4.2.0]oct-2-ene-2-carboxylate trifluoroacetate was added in a single portion. After 3 h the reaction mixture was poured on diethyl ether. The solid material was collected by filtration and triturated with ethyl acetate.

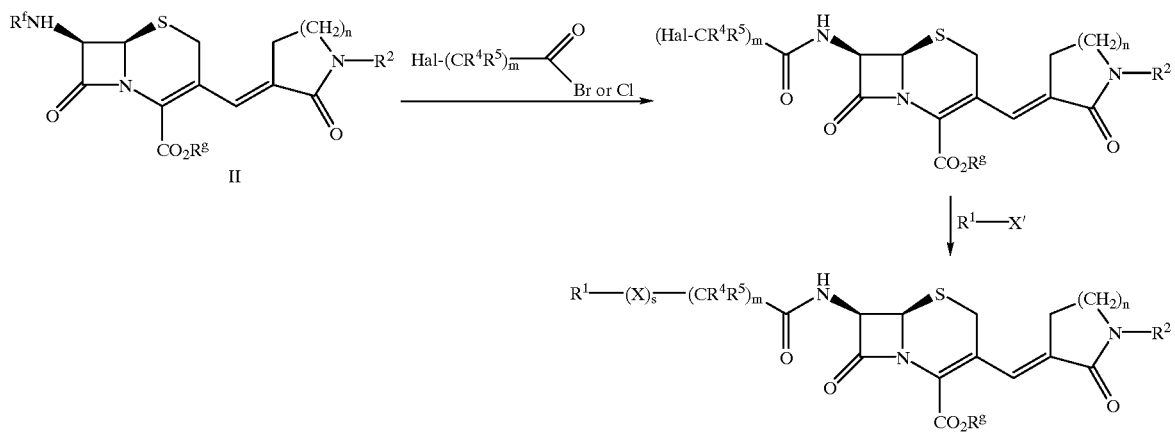

Scheme 2, embodiment (b)

wherein X is O, S, NH and X' accordingly OH or O⁻, SH or S⁻ or NH₂ and the remaining substituent are as defined above.

EXAMPLES

Example 1
(E)-(6R,7R)-3-[1-[1-[(4-Hydroxy-phenylcarbamoyl)-methyl]-pyridin-1-ium-4-ylmethyl]-2-oxo-pyrrolidin-3-ylidenemethyl]-8-oxo-7-[2-(2,4,5-trichlorophenylsulfanyl)-acetylamino]-5-thia-1-aza-bicyclo[4.2.0]oct-2-ene-2-carboxylate Yield: 112.0 mg (67.5%) beige powder
IR(KBr): 1770, 1678, 1642 cm⁻¹
MS(ISP): 790.2 (M+)

According to the procedure in Example 1 the following additional compounds were prepared:

Example 2
(E)-(6R,7R)-3-[1-[1-[(4-Hydroxy-phenylcarbamoyl)-methyl]-pyridin-1-ium-4-ylmethyl]-2-oxo-pyrrolidin-3-ylidenemethyl]-8-oxo-7-[2-(1-benzothiazol- 2-ylsulfanyl)-acetylamino]-5-thia-1-aza-bicyclo[4.2.0]oct-2-ene-2-carboxylate

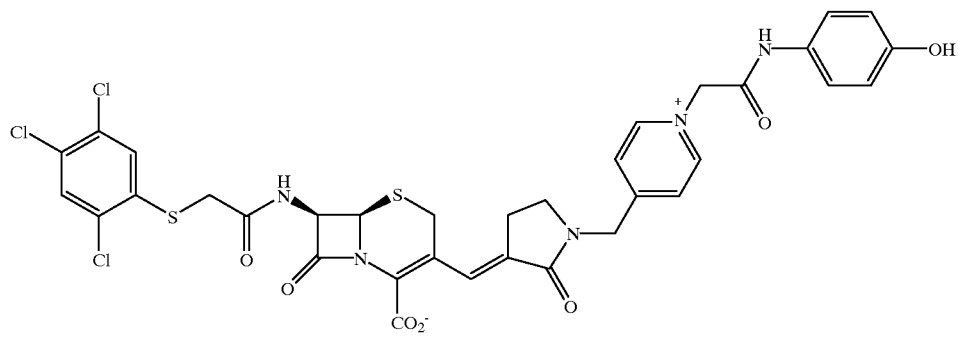

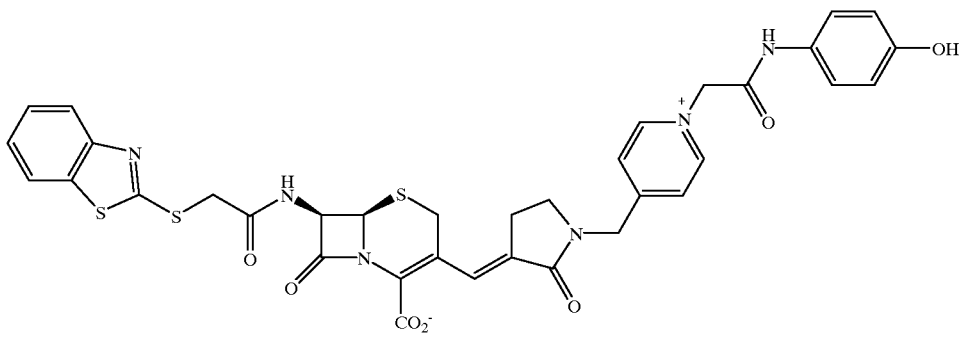

With 70.0 mg (0.43 mmol) 1,1'-carbonyldiimidazole, 96.0 mg (0.43 mmol) (benzothiazol-2-ylsulfanyl)-acetic acid and 233.8 mg (0.36 mmol) (E)-(6R,7R)-7-amino-3-[1-[1-[(4-hydroxy-phenylcarbamoyl)-methyl]-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate trifluoroacetate in 4 ml N,N-dimethylacetamide.

Yield: 92.0 mg (34.4%) yellow powder
IR(KBr): 1769, 1679, 1643, 1625 cm$^{-1}$
MS(ISP): 743.3 (M+H$^{+m}$)

Example 3
(E)-(6R,7R)-7-[2-(Benzothiazol-2-ylsulfanyl)-acetylamino]-3-(1-cyclopropyl-methyl-2-oxo-pyrrolidin-3-ylidenemethyl)-8-oxo-5-thia-1-aza-bicyclo[4.2.0]-oct-2-ene-2-carboxylic acid With 220.0 mg (1.35 mmol) 1,1'-carbonyldiimidazole, 304.1 mg (1.35 mmol) (benzothiazol-2-ylsulfanyl)-acetic acid and 394.8 mg (1.13 mmol) (E)-(6R,7R)-7-amino-3-(1-cyclopropylmethyl-2-oxo-pyrrolidin-3-ylidenemethyl)-8-oxo-5-thia-1-azabicyclo[4.2.0]oct-2-ene-2-carboxylic acid in 7 ml N,N-dimethylformamide.

Yield: 173.0 mg (27.5%) orange powder
IR(KBr): 1772, 1665, 1623 cm$^{-1}$
MS(ISP): 557.1 (M+H$^{+}$)

Example 4
(E)-(6R,7R)-3-[1-[1-[(4-Hydroxy-phenylcarbamoyl)-methyl]-pyridin-1-ium-4-ylmethyl]-2-oxo-pyrrolidin-3-ylidenemethyl]-8-oxo-7-[2-(pyridin-4-yl-sulfanyl)-acetylamino]-5-thia-1-aza-bicyclo[4.2.0]oct-2-ene-2-carboxylate

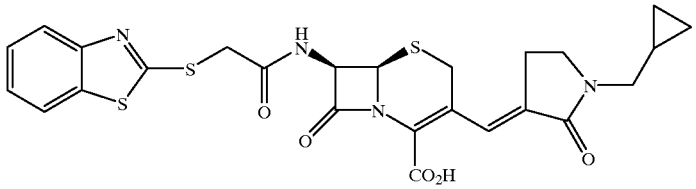

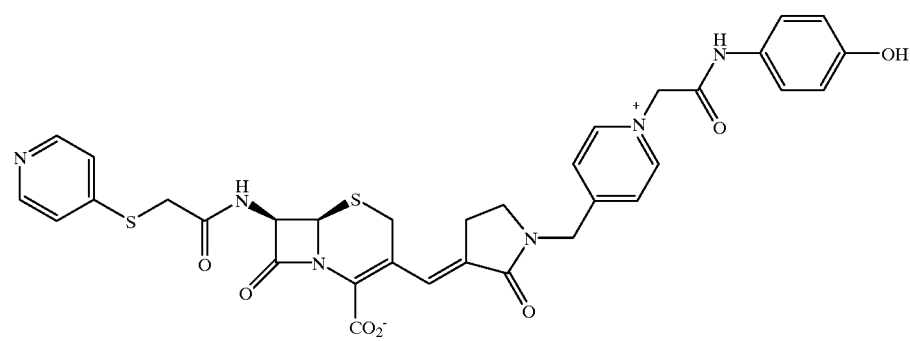

With 70.0 mg (0.43 mmol) 1,1'-carbonyldiimidazole, 72.8 mg (0.43 mmol) (pyridin-4-ylsulfanyl)-acetic acid and 232.8 mg (0.36 mmol) (E)-(6R,7R)-7-amino-3-[1-[1-[(4-hydroxy-phenylcarbamoyl)-methyl]-pyridin-1-ium-4-yl-methyl]-2-oxo-pyrrolidin-3-ylidenemethyl]-8-oxo-5-thia-1-aza-bicyclo[4.2.0]oct-2-ene-2-carboxylate trifluoroacetate in 4 ml N,N-dimethylacetamide. The brown solid was purified by column chromatography on MCI gel (75–150μ, Mitsubishi Kasei Corporation) with a gradient of water: acetonitrile (1:0, 4:1, 3:1, 2:1, 1:1). The organic solvent was stripped off at a rotary evaporator and the aqueous phase was freeze-dried.

Yield: 58.0 mg (30.0%) beige lyophilisate
IR(KBr): 1772, 1670, 1625 cm$^{-1}$
MS(ISP): 687.3 (M+H$^+$)

Example 5

(E)-(6R,7R)-3-[1-[1-[(3-Fluoro-4-hydroxy-phenylcarbamoyl)-methyl]-pyridin-1-ium-4-ylmethyl]-2-oxo-pyrrolidin-3-ylidenemethyl]-7-[2 -(naphthalen-2-ylsulfanyl)-acetylamino]-8-oxo-5-thia-1-aza-bicyclo[4.2.0]oct-2-ene-2-carboxylate of water: acetonitrile (1:0, 4:1, 3:1, 2:1, 1:1). The organic solvent was stripped off at a rotary evaporator and the aqueous phase was freeze-dried.

Yield: 55.0 mg (24.0%) beige lyophilisate

IR(KBr): 1770, 1680, 1650, 1628 cm$^{-1}$

MS(ISP): 754.3 (M+H$^+$)

Example 6

(E)-(6R,7R)-3-[1-(3-Hydroxy-benzyl)-2-oxo-pyrrolidin-3-ylidenemethyl]-8-oxo-7-[2-(2,4,5-trichloro-phenylsulfanyl)-acetylamino]-5-thia-1-aza-bicyclo[4.2.0]oct-2-ene-2-carboxylic acid

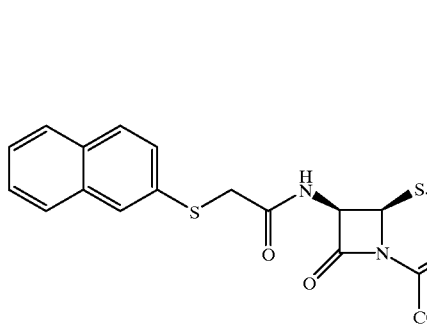

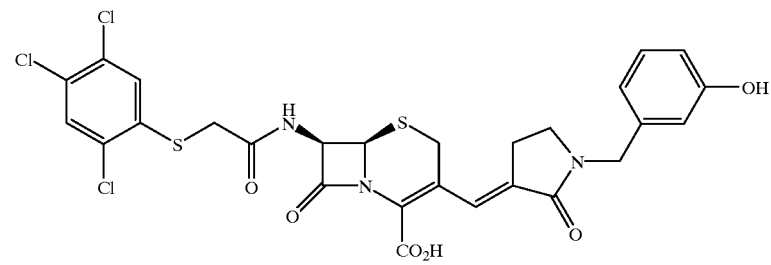

With 58.3 mg (0.36 mmol) 1,1'-carbonyldiimidazole, 78.5 mg (0.36 mmol) (naphthalen-2-ylsulfanyl)-acetic acid and 200.0 mg (0.30 mmol) (E)-(6R,7R)-7-amino-3-[1-[1-[(3-fluoro-4-hydroxy-phenylcarbamoyl)-methyl]-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate trifluoroacetate in 4 ml N,N-dimethylacetamide. The resulting solid was purified by column chromatography on MCI gel (75–150μ, Mitsubishi Kasei Corporation) with a gradient With 146.0 mg (0.90 mmol) 1,1'-carbonyldiimidazole, 244.4 mg (0.90 mmol) (2,4,5-trichloro-phenylsulfanyl)-acetic acid and 301.0 mg (0.73 mmol) (E)-(6R,7R)-7-amino-3-[1-(3-hydroxy-benzyl)-2-oxo-pyrrolidin-3-ylidenemethyl]-8-oxo-5-thia-1-aza-bicyclo[4.2.0]oct-2-ene-2-carboxylic acid trifluoroacetate in 5 ml N,N-dimethylacetamide.

Yield: 180.0 mg (37.7%) beige powder

IR(KBr): 1767, 1664, 1614 cm$^{-1}$

MS(ISP): 654.1 (M+H$^+$)

Example 7

(E)-(6R,7S)-3-[1-(3-Hydroxy-benzyl)-2-oxo-pyrrolidin-3-ylidenemethyl]-8-oxo-7-[2-naphthalen-2-ylsulfanyl)-acetylamino]-5-thia-1-aza-bicyclo[4.2.0]oct-2-ene-2-carboxylic acid

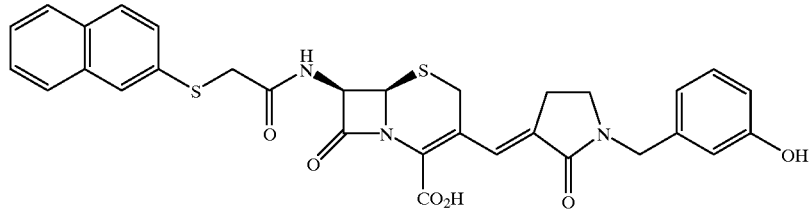

With 146.0 mg (0.90 mmol) 1,1'-carbonyldiimidazole, 196.5 mg (0.90 mmol) (naphthalen-2-ylsulfanyl)-acetic acid and 301.0 mg (0.73 mmol) (E)-(6R,7R)-7-amino-3-[1-(3-hydroxy-benzyl)-2-oxo-pyrrolidin-3-ylidenemethyl]-8-oxo-5-thia-1-aza-bicyclo[4.2.0]oct-2-ene-2-carboxylic acid trifluoroacetate in 5 ml N,N-dimethylacetamide. The resulting solid was purified by column chromatography on MCI gel (75–150μ, Mitsubishi Kasei Corporation) with a gradient of water: acetonitrile (1:0, 4:1, 3:1, 2:1, 1:1). The organic solvent was stripped off at a rotary evaporator and the aqueous phase was freeze-dried.

Yield: 65.0 mg (14.6%) beige lyophilisate
IR(KBr): 1771, 1663, 1589 cm$^{-1}$

MS(ISP): 602.2 (M+H$^+$)

Example 8

Mixture of (E)-(6R,7R)-8-oxo-3-[(R)- and -[(S)-2-oxo-[1,3']bipyrrolidinyl-3-ylidenemethyl]-8-oxo-7-[2-(2,4,5-trichloro-phenylsulfanyl)-acetylamino]-5-thia-1-aza-bicyclo[4.2.0]oct-2-ene-2-carboxylic acid hydrochloride

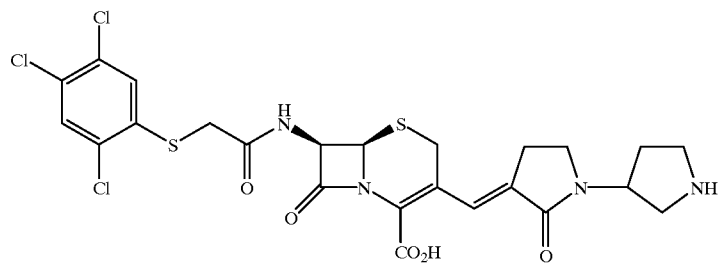

Step a: Mixture of (E)-(6R,7R)-3-[(R)- and -[(S)-1'-allyloxycarbonyl-2-oxo-[1,3']bipyrrolidinyl-3-ylidenemethyl]-8-oxo-7-[2-(2,4,5-trichloro-phenylsulfanyl)-acetylamino]-5-thia-1-aza-bicyclo[4.2.0]oct-2-ene-2-carboxylic acid

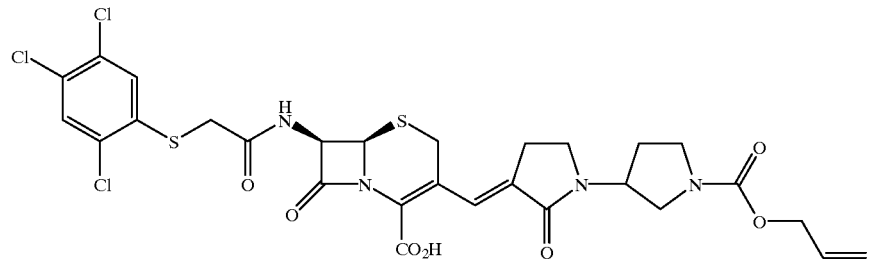

With 115.2 mg (0.71 mmol) 1,1'-carbonyldiimidazole, 193.4 mg (0.71 mmol) (2,4,5-trichloro-phenylsulfanyl)-acetic acid and 329.1 mg (0.59 mmol) of a mixture of (E)-(6R,7R)-3-[(R)- and -[(S)-1'-allyloxycarbonyl-2-oxo-[1,3']bipyrrolidin-3-ylidenemethyl)-7-amino-8-oxo-5-thia-1-aza-bicyclo[4.2.0]oct-2-ene-2-carboxylic acid trifluoroacetate in 6 ml N,N-dimethylacetamide Prepared according to example A1.

Yield: 220.0 mg (66.0%) beige powder
IR(KBr): 1774, 1678, 1624 cm$^{-1}$
MS(ISP): 703.2 (M+H$^+$)

Step b: Mixture of (E)-(6R,7R)-8-oxo-3-[(R)- and -[(S)-2-oxo-[1,3']bi-pyrrolidinyl-3-ylidenemethyl]-8-oxo-7-[2-(2,4,5-trichloro-phenylsulfanyl)-acetylamino]- 5-thia-1-aza-bicyclo[4.2.0]oct-2-ene-2-carboxylic acid hydrochloride The product prepared in step a (220.0 mg, 0.31 mmol) was suspended in 12 ml dichloromethane and 124 µl (0.50 mmol) N,O-bis-(trimethylsilyl)-acetamide was added. After a clear solution had formed, 5.60 mg (8.56 µmol) palladium-bis-(triphenylphosphine)-dichloride, 0.36 ml (6.30 mmol) acetic acid and 0.8 ml (3.0 mmol) tributyltinhydride were added. After 45 min 40 µl water was added to the suspension and the reaction mixture was poured under stirring on 200 ml diethyl ether, containing 2 ml of a hydrochloric acid-saturated diethyl ether solution. The solid was collected by filtration and triturated with 40 ml ethyl acetate.

Yield: 180.0 mg (87.8%) beige powder
IR(KBr): 1771, 1661, 1582 cm$^{-1}$
MS(ISP): 619.1 (M+H+)

Example 9

(E)-(6R,7R)-3-[1-[1-[(3-Fluoro-4-hydroxy-phenylcarbamoyl)-methyl]-pyridin-1-ium-4-ylmethyl]-2-oxo-pyrrolidin-3-ylidenemethyl]-8-oxo-7-(2-phenylsulfanyl-acetylamino)-5-thia-1-aza-bicyclo[4.2.0]oct-2-ene-2-carboxylate With 175.0 mg (1.08 mmol) 1,1'-carbonyldiimidazole, 182.0 mg (1.08 mmol) 2-(phenylthio)acetic acid and 500.0 mg (0.75 mmol) (E)-(6R,7R)-7-amino-3-[1-[1-[(3-fluoro-4-hydroxy-phenylcarbamoyl)-methyl]-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate trifluoroacetate in 4 ml N,N-dimethylacetamide. The resulting solid was purified by column chromatography on MCI gel (75–150µ, Mitsubishi Kasei Corporation) with a gradient of water: acetonitrile (1:0, 4:1, 3:1, 2:1). The organic solvent was stripped off at a rotary evaporator and the aqueous phase was freeze-dried.

Yield: 90.0 mg (20.6%) beige lyophilisate
IR(KBr): 1772, 1680, 1648 cm$^{-1}$
MS(ISP): 704.4 (M +)

Example 10

(E)-(6R,7R)-7-[2-(2,5-Dichloro-phenylsulfanyl)-acetylamino]-3-[1-[(3-fluoro-4-hydroxy-phenylcarbamoyl)-methyl]-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate

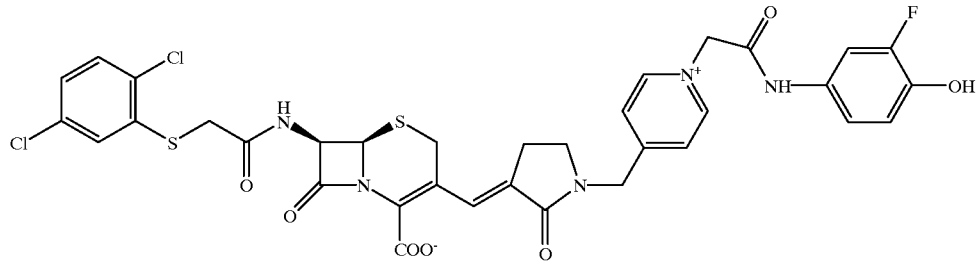

With 72.9 mg (0.45 mmol) 1,1'-carbonyldiimidazole, 106.5 mg (0.45 mmol) (2,5-dichloro-phenylsulfanyl)acetic acid and 250.0 mg (0.37 mmol) (E)-(6R,7R)-7-amino-3-[1-[1-[(3-fluoro-4-hydroxy-phenylcarbamoyl)-methyl]-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate trifluoroacetate in 4 ml N,N-dimethylacetamide. The resulting solid was purified by column chromatography on MCI gel (75–150µ, Mitsubishi Kasei Corporation) with a gradient of water: acetonitrile (1:0, 4:1, 3:1, 2:1, 1:1). The organic solvent was stripped off at a rotary evaporator and the aqueous phase was freeze-dried.

Yield: 74.5 mg (21.3%) beige lyophilisate
IR(KBr): 1772, 1680, 1650 cm$^{-1}$
MS(ISP): 772.3 (M+H$^+$)

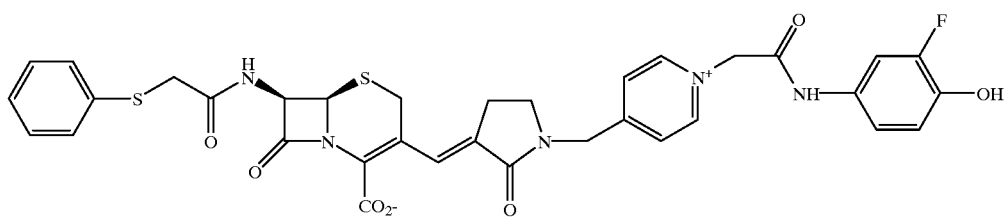

Example 11
(E)-(6R,7R)-8-Oxo-3-[(R)-2-oxo-[1,3']bipyrrolidinyl-3-ylidenemethyl]-7-(2-phenylsulfanyl-acetylamino)-5-thia-1-aza-bicyclo[4.2.0]oct-2-ene-2-carboxylic acid hydrochloride (1:1)

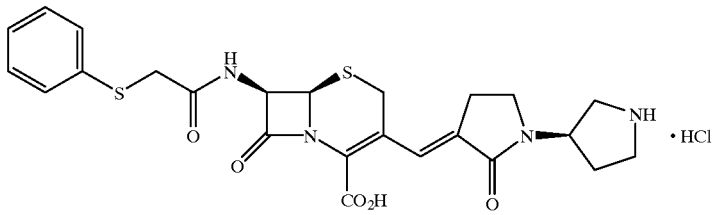

(E)-(6R,7R)-3-[(R)-1'-allyloxycarbonyl-2-oxo-[1,3']bipyrrolidinyl-3-ylidenemethyl]-8-oxo-7-(2-phenylsulfanyl-acetylamino)-5-thia-1-aza-bicyclo[4.2.0]oct-2-ene-2-carboxylic acid (370.0 mg, 0.62 mmol) was dissolved in 20 ml dichloromethane and treated successively with bis(triphenylphosphine)palladium(II) chloride (10.9 mg, 0.015 mmol), acetic acid (0.71 ml, 12.4 mmol) and tributyltin hydride (1.67 ml, 6.20 mmol). After 40 min, the suspension was poured on 250 ml diethyl ether containing 3 ml of a hydrochloric acid-saturated diethyl ether solution and stirred for 1 h. The suspension was filtered, the solid material was triturated with ethyl acetate for 1h and dried in high vacuum.

Yield: 25.5% beige solid
MS(ISP): 515.3 (M+H)$^+$
IR(KBr): 1776, 1666, 1632 cm$^{-1}$

Example 12
(E)-(6R,7R)-3-(1-Cyclopropyl-2-oxo-pyrrolidin-3-ylidenemethyl)-7-[2-(naphthalen-2-ylsulfanyl)-acetylamino]-8-oxo-5-thia-1-aza-bicyclo[4.2.0]oct-2-ene-2-carboxylic acid imidazole salt (1:1)

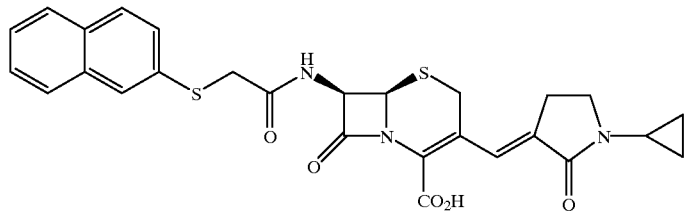

Yield: 42.6 % beige solid
MS(ISP): 536.3 (M+H)$^+$
IR(KBr): 1769, 1664, 1624 cm$^{-1}$

Example 13
(E)-(6R,7R)-3-[1-(4-Hydroxy-phenyl)-2-oxo-pyrrolidin-3-ylidenemethyl]-7-[2-(naphthalene-2-ylsulfanyl)-acetylamino]-8-oxo-5-thia-1-aza-bicyclo[4.2.0]oct-2-ene-2-carboxylic acid sodium salt (1:1)

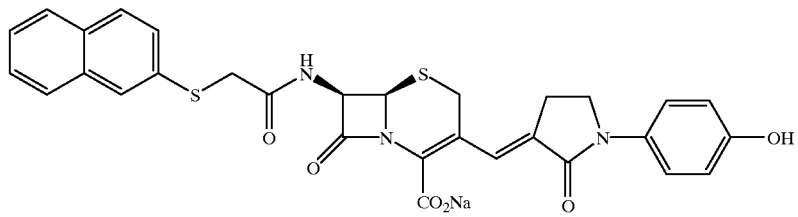

With 140.0 mg (0.86 mmol) 1,1'-carbonyldiimidazole, 187.7 mg (0.86 mmol) (2-naphthylthio)acetic acid and 230.0 mg (0.60 mmol) (E)-(6R,7R)-7-amino-3-[1-(4-hydroxy-phenyl)-2-oxo-pyrrolidin-3-ylidenemethyl]-8-oxo-5-thia-1-aza-bicyclo[4.2.0]oct-2-ene-2-carboxylic acid in 4 ml N,N'-dimethylacetamide. The resulting yellow solid was suspended in 3 ml water and converted into its sodium salt by treatment with 500 μl 1M NaOH. The solution was chromatographed on MCI gel with a gradient of water:acetonitrile (1:0, 9:1). The organic solvent was stripped off at a rotary evaporator and the aqueous phase was freeze-dried.

Yield: 46.0 % yellow lyophilisate
MS(ISP): 588.3 (M+H)$^+$
IR(Nujol): 1761, 1659, 1591 cm$^1$ Example 14
(E)-(6R,7R)-8-Oxo-3-[2-oxo-1-(4-sulfamoyl-benzyl)-pyrrolidin-3-ylidenemethyl]-7-[2-phenylsulfanyl)-acetylamino]-5-thia-1-aza-bicyclo[4.2.0]oct-2-ene-2-carboxylic acid

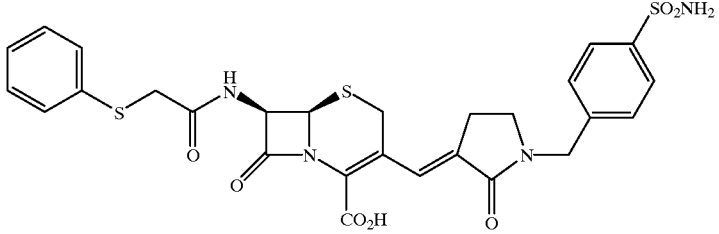

Yield: 75.3 % beige solid
MS(ISN): 613.2 (M−H)$^−$
IR(KBr): 1770, 1667, 1602 cm$^{-1}$ The following example illustrates pharmaceutical preparations containing an antimicrobial composition provided by the present invention:

Example A

Production of dry ampoules for parenteral administration:
A mixture of 0,25-8 g of vinyl-pyrrolidinone cephalosporin derivative and 0,25-8 g carbapenem antibiotic or 0,25-8 g β-lactamase inhibitor is prepared in the usual manner and filled into an ampoule as
a) mixtures of dry powders (crystalline, amorphous or lyophilisates powder) of vinyl-pyrrolidinone cephalosporin derivative and carbapenem antibiotic or β-lactamase inhibitor; or
b) lyophilisates of the mixed solutions of vinyl-pyrrolidinone cephalosporin derivative and carbapenem antibiotic or β-lactamase inhibitor.

The dry powders (crystalline, amorphous or lyophilisates powder) of vinyl-pyrrolidinone cephalosporin derivative and carbapenem antibiotic or β-lactamase inhibitor can be filled in separate ampoules and mixed prior to the administration.

What is claimed is:
1. A pharmaceutical composition comprising an antimicrobially effective amount of a first compound selected from the group consisting of

(E)-(6R,7R)-3-[1-[1-[(4-Hydroxy-phenylcarbamoyl)-methyl]-pyridin-1-ium-4-ylmethyl]-2-oxo-pyrrolidin-3-ylidenemethyl]-8-oxo-7-[2-(2,4,5-trichloro-phenylsulfanyl)-acetylamino]-5-thia-1-aza-bicyclo[4.2.0]oct-2-ene-2-carboxylate;

(E)-(6R,7R)-3-[1-[1-[(4-Hydroxy-phenylcarbamoyl)-methyl]-pyridin-1-ium-4-ylmethyl]-2-oxo-pyrrolidin-3-ylidenemethyl]-8-oxo-7-[2-(]-benzothiazol-2-ylsulfanyl)-acetylamino]-5-thia-1-aza-bicyclo[4.2.0]oct-2-ene-2-carboxylate;

(E)-(6R,7R)-7-[2-(Benzothiazol-2-ylsulfanyl)-acetylamino]-3-(1-cyclopropylmethyl-2-oxo-pyrrolidin-3-ylidenemethyl)-8-oxo-5-thia-1-aza-bicyclo[4.2.0]oct-2-ene-2-carboxylic acid;

(E)-(6R,7R)-3-[1-[1-[(4-Hydroxy-phenylcarbamoyl)-methyl]-pyridin-1-ium-4-ylmethyl]-2-oxo-pyrroidin-3-ylidenemethyl]-8-oxo-7-[2-(pyridin-4-ylsulfanyl)-acetylamino]-5-thia-1-aza-bicyclo[4.2.0]oct-2-ene-2-carboxylate;

(E)-(6R,7R)-3-[1-[1-[(3-Fluoro-4-hydroxy-phenylcarbamoyl)-methyl]-pyridin-1-ium-4-ylmethyl]-2-oxo-pyrrolidin-3-ylidenemethyl]-7-[2-(naphthalen-2-ylsulfanyl)-acetylamino]-8-oxo-5-thia-1-aza-bicyclo[4.2.0]oct-2-ene-2-carboxylate;

(E)-(6R,7R)-3-[1-(3-Hydroxy-benzyl)-2-oxo-pyrrolidin-3-ylidenemethyl]-8-oxo-7-[2-(2,4,5-trichloro-phenylsulfanyl)-acetylamino]-5-thia-1-aza-bicyclo[4.2.0]oct-2-ene-2-carboxylic acid;

(E)-(6R,7S)-3-[1-(3-Hydroxy-benzyl)-2-oxo-pyrrolidin-3-ylidenemethyl]-8-oxo-7-[2-naphthalen-2-ylsulfanyl)-acetylamino]-5-thia-1-aza-bicyclo[4.2.0]oct-2-ene-2-carboxylic acid;

(E)-(6R,7R)-3-[(R)- and -[(S)-2-oxo-[1,3']Bipyrrolidinyl-3-ylidene-methyl]-8-oxo-7-[2-(2,4,5-trichloro-phenylsulfanyl)-acetylamino]-5-thia-1-aza-bicyclo[4.2.0]oct-2-ene-2-carboxylic acid hydrochloride;

(E)-(6R,7R)-3-[1-[1-[(3-Fluoro-4-hydroxy-phenylcarbamoyl)-methyl]-pyridin-1-ium-4-ylmethyl]-2-oxo-pyrrolidin-3-ylidenemethyl]-8-oxo-7-(2-phenylsulfanyl-acetylamino)-5-thia-1-aza-bicyclo[4.2.0]oct-2-ene-2-carboxylate;

(E)-(6R,7R)-7-[2-(2,5-Dichloro-phenylsulfanyl)-acetylamino]-3-[1-[(3-fluoro-4-hydroxy-phenylcarbamoyl)-methyl]-pyridin-1-ium-4-yl ethyl]-2-oxo-pyrrolidin-3-ylidenemethyl]-8-oxo-5-thia-1-aza-bicyclo[4.2.0]oct-2-ene-2-carboxylate;

(E)-(6R,7R)-8-oxo-3-[(R)-2-oxo-[1,3']Bipyrrolidinyl-3-ylidenemethyl]-7-[2-(phenylsulfanyl)-acetylamino]-5-thia-1-aza-bicyclo[4.2.0]oct-2-ene-2-carboxylic acid hydrochloride;

(E)-(6R,7R)-3-(1-Cyclopropyl-2-oxo-pyrrolidin-3-ylidenemethyl)-7-[2-(naphthalene-2-ylsulfanyl)-acetylamino]-8-oxo-5-thia-1-aza-bicyclo[4.2.0]oct-2-ene-2-carboxylic acid;

(E)-(6R,7R)-3-[1-(4-Hydroxy-phenyl)-2-oxo-pyrrolidin-3-ylidenemethyl]-7-[2-(naphthalene-2-ylsulfanyl)-acetylamino]-8-oxo-5-thia-1-aza-bicyclo[4.2.0]oct-2-ene-2-carboxylic acid sodium salt (1:1); and (E)-(6R,7R)-8-Oxo-3-[2-oxo-1-(4-sulfamoyl-benzyl)-pyrrolidin-3-ylidenemethyl]-7-[2-phenylsulfanyl)-acetylamino]-5-thia-1-aza-bicyclo[4.2.0]oct-2-ene-2-carboxylic acid;

as well as readily hydrolyzable esters thereof and their hydrates and pharmaceutically acceptable salts thereof and their hydrates;

and a second compound selected from the group consisting of carbapenem antibiotics and pharmaceutically acceptable salts thereof and β-lactamase inhibitors and phamaceutically acceptable salts thereof; and a therapeutically inert carrier.

2. The composition of claim 1 wherein the second compound is selected from the group consisting of meropenem, imipenem, tazobactain, sulbactam, clavulanic acid and (Z)-(2S,3S,5R)-3-(2-cyanoethenyl)-3-methyl-4,4,7-trioxo-4-thia-1-aza-bicyclo[3.2.0]heptane-2-carboxylic acid.

3. The composition of claim 1, wherein the ratio by weight of the first compound to the second compound is from about 1:20 to about 20:1.

4. The composition of claim 2 wherein the first compound is (E)-(6R,7R)-3-[1-[1-[(4-Hydroxy-phenylcarbamoyl)-methyl]-pyridin-1-ium-4-ylmethyl]-2-oxo-pyrrolidin-3-ylidenemethyl]-8-oxo-7-[2-(2,4,5-trichloro-phenylsulfanyl)-acetylamino]-5-thia-1-aza-bicyclo[4.2.0]oct-2-ene-2-carboxylate.

5. The composition of claim 2 wherein the first compound is (E)-(6R,7R)-3-[1-[1-[(4-Hydroxy-phenylcarbamoyl)-methyl]-pyridin-1ium-4-ylmethyl]-2-oxo-pyrroidin-3-ylidenemethyl]-8-oxo-7-[2-(1-benzothiazol-2-ylsulfanyl)-acetylamino]-5-thia-1-aza-bicyclo[4.2.0]oct-2-ene-2-carboxylate.

6. A composition of claim 2 wherein the first compound is (E)-(6R,7R)-7-[2-(Benzothiazol-2-ylsulfanyl)-acetylamino]-3-(1-cyclopropylmethyl-2-oxo-pyrrolidin-3-ylidenemethyl)-8-oxo-5-thia-1-aza-bicyclo[4.2.0]oct-2-ene-2-carboxylic acid.

7. The composition of claim 2 wherein the first compound is (E)-(6R,7R)-3-[1-[1-[(4-Hydroxy-phenylcarbamoyl)-methyl]-pyridin-1-ium-4-ylmethyl]-2-oxo-pyrrolidin-3-ylidenemethyl]-8-oxo-7-[2-(pyridin-4-ylsulfanyl)-acetylamino]-5-thia-1-aza-bicyclo[4.2.0]oct-2-ene-2-carboxylate.

8. The composition of claim 2 wherein the first compound is (E)-(6R,7R)-3-[1-[1-[(3-Fluoro-4-hydroxy-phenylcarbamoyl)-methyl]-pyridin-1-ium-4-ylmethyl]-2-oxo-pyrrolidin-3-ylidenemethyl]-7-[2-(naphthalen-2-ylsulfanyl)-acetylamino]-8-oxo-5-thia-1-aza-bicyclo[4.2.0]oct-2-ene-2-carboxylate.

9. The composition of claim 2 wherein the first compound is (E)-(6R,7R)-3-[1-(3-Hydroxy-benzyl)-2-oxo-pyrrolidin-3-ylidenemethyl]-8-oxo-7-[2-(2,4,5-trichloro-phenylsulfanyl)-acetylamino]-5-thia-1-aza-bicyclo[4.2.0]oct-2-ene-2-carboxylic acid.

10. The composition of claim 2 wherein the first compound is (E)-(6R,7S)-3-[1-(3-Hydroxy-benzyl)-2-oxo-pyrrolidin-3-ylidenemethyl]-8-oxo-7-[2-naphthalen-2-ylsulfanyl)-acetylamino]-5-thia-1-aza-bicyclo[4.2.0]oct-2-ene-2-carboxylic acid.

11. The composition of claim 2 wherein the first compound is (E)-(6R,7R)-3-[(R)- and -[(S)-2-oxo-[1,3'] Bipyrrolidinyl-3-ylidene-methyl]-8-oxo-7-[2-(2,4,5-trichloro-phenylsulfanyl)-acetylamino]-5-thia-1-aza-bicyclo[4.2.0]oct-2-ene-2-carboxylic acid hydrochloride.

12. The composition of claim 2 wherein the first compound is (E)-(6R,7R)-3-[1-[1-[(3-Fluoro-4-hydroxy-phenylcarbamoyl)-methyl]-pyridin-1-ium-4-ylinethyl]-2-oxo-pyrrolidin-3-ylidenemethyl]-8-oxo-7-(2-phenylsulfanyl-acetylamino)-5-thia-1-aza-bicyclo[4.2.0]oct-2-ene-2-carboxylate.

13. The composition of claim 2 wherein the first compound is (E)-(6R,7R)-7-[2-(2,5-Dichloro-phenyl-sulfanyl)-acetylamino]-3-[1-[(3-fluoro-4-hydroxy-phenylcarbamoyl)-methyl]-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate.

14. The composition of claim 2 wherein the first compound is (E)-(6R,7R)-8-oxo-3-[(R)-2-oxo-[1,3'] Bipyrrolidinyl-3-ylidenemethyl]-7-[2-(phenylsulfanyl)-acetylamino]-5-thia-1-aza-bicyclo[4.2.0]oct-2-ene-2-carboxylic acid hydrochloride.

15. The composition of claim 2 wherein the first compound is (E)-(6R,7R)-3-(1-Cyclopropyl-2-oxo-pyrrolidin-3-ylidenemethyl)-7-[2-(naphthalene-2-ylsulfanyl)-acetylamino]-8-oxo-5-thia-1-aza-bicyclo[4.2.0]oct-2-ene-2-carboxylic acid.

16. The composition of claim 2 wherein the first compound is (E)-(6R,7R)-3-[1-(4-Hydroxy-phenyl)-2-oxo-pyrrolidin-3-ylidenemethyl]-7-[2-(naphthalene-2-ylsulfanyl)-acetylaminio]-8-oxo-5-thia-1-aza-bicyclo[4.2.0]oct-2-ene-2-carboxylic acid sodium salt (1:1).

17. The composition of claim 2 wherein the first compound is (E)-(6R,7R)-8-Oxo-3-[2-oxo-1-(4-sulfamoyl-benzyl)-pyrrolidin-3-ylidenemethyl]-7-[2-phenylsulfanyl)-acetylamino]-5-thia-1-aza-bicyclo[4.2.0]oct-2-ene-2-carboxylic acid.

\* \* \* \* \*

UNITED STATES PATENT AND TRADEMARK OFFICE
CERTIFICATE OF CORRECTION

PATENT NO. : 6,150,350
DATED : November 21, 2000
INVENTOR(S) : Peter Angehrn, Ingrid Heinze-Krauss, Malcolm Page, Hans G.F. Richter It is certified that error appears in the above-identified patent and that said Letters Patent is hereby corrected as shown below:

Column 36, claim 1,
Line 3, "[2-( ]-benzothiazol-2-" should read -- [2-(1-benzothiazol-2- --.

Column 37, claim 2,
Line 15, "tazobactain" should read -- tazobactam --.

Signed and Sealed this

Twentieth Day of November, 2001

*Attest:*

NICHOLAS P. GODICI
*Attesting Officer*  Acting Director of the United States Patent and Trademark Office